(12) United States Patent
June et al.

(10) Patent No.: US 11,890,301 B2
(45) Date of Patent: Feb. 6, 2024

(54) METHODS AND COMPOSITIONS FOR CELLS EXPRESSING A CHIMERIC INTRACELLULAR SIGNALING MOLECULE

(71) Applicants: The Trustees of the University of Pennsylvania, Philadelphia, PA (US); Wayne State University, Detroit, MI (US)

(72) Inventors: Carl H. June, Merion Station, PA (US); Michael Milone, Cherry Hill, NJ (US); Yangbing Zhao, Lumberton, NJ (US); Lawrence G. Lum, Charlottesville, VA (US); Archana Thakur, Charlottesville, VA (US)

(73) Assignees: The Trustees of the University of Pennsylvania, Philadelphia, PA (US); Wayne State University, Detroit, MI (US)

( * ) Notice: Subject to any disclaimer, the term of this patent is extended or adjusted under 35 U.S.C. 154(b) by 433 days.

(21) Appl. No.: 15/754,227

(22) PCT Filed: Aug. 26, 2016

(86) PCT No.: PCT/US2016/049087
§ 371 (c)(1),
(2) Date: Feb. 21, 2018

(87) PCT Pub. No.: WO2017/040324
PCT Pub. Date: Mar. 9, 2017

(65) Prior Publication Data
US 2018/0243341 A1    Aug. 30, 2018

Related U.S. Application Data

(60) Provisional application No. 62/211,311, filed on Aug. 28, 2015.

(51) Int. Cl.
| | | |
|---|---|---|
| *C12N 15/85* | (2006.01) | |
| *C07K 16/32* | (2006.01) | |
| *C12N 15/09* | (2006.01) | |
| *A61K 35/17* | (2015.01) | |
| *C07K 16/28* | (2006.01) | |
| *A61P 35/00* | (2006.01) | |
| *C07K 14/705* | (2006.01) | |
| *C07K 14/725* | (2006.01) | |
| *C12N 5/0783* | (2010.01) | |
| *A61K 35/00* | (2006.01) | |
| *A61K 39/00* | (2006.01) | |

(52) U.S. Cl.
CPC .............. *A61K 35/17* (2013.01); *A61P 35/00* (2018.01); *C07K 14/7051* (2013.01); *C07K 14/70517* (2013.01); *C07K 14/70578* (2013.01); *C07K 16/2803* (2013.01); *C07K 16/2809* (2013.01); *C07K 16/2863* (2013.01); *C07K 16/2887* (2013.01); *C07K 16/32* (2013.01); *C12N 5/0636* (2013.01); *A61K 35/00* (2013.01); *A61K 39/0011* (2013.01); *A61K 2039/5156* (2013.01); *A61K 2039/5158* (2013.01); *C07K 2317/24* (2013.01); *C07K 2317/31* (2013.01); *C07K 2317/622* (2013.01); *C07K 2319/02* (2013.01); *C07K 2319/03* (2013.01); *C07K 2319/33* (2013.01); *C07K 2319/43* (2013.01); *C07K 2319/50* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,229,275 A | 7/1993 | Goroff et al. |
| 5,350,674 A | 9/1994 | Boenisch et al. |
| 5,565,332 A | 10/1996 | Hoogenboom et al. |
| 5,567,610 A | 10/1996 | Borrebaeck et al. |
| 5,585,089 A | 12/1996 | Queen et al. |
| 5,585,362 A | 12/1996 | Wilson et al. |
| 5,731,168 A | 3/1998 | Carter et al. |
| 6,004,554 A | 12/1999 | Thorpe |

(Continued)

FOREIGN PATENT DOCUMENTS

| | | |
|---|---|---|
| CN | 1878867 A | 12/2006 |
| CN | 103492406 A | 1/2014 |

(Continued)

OTHER PUBLICATIONS

Waller and Boyer, New strategies in allogeneic stem cell transplantation: immunotherapy, Bone Marrow Transplantation (2000) 25, Suppl. 2, S20-S24 using irradiated allogeneic T cells.*

(Continued)

*Primary Examiner* — Maria Marvich
(74) *Attorney, Agent, or Firm* — Saul Ewing LLP; Kathryn Doyle

(57) ABSTRACT

The present invention relates to compositions and methods for enhancing T cell metabolism and activity for more effective adoptive T cell therapy. By expressing an chimeric antigen receptor and bispecific antibodies in T cells, the T cells are metabolically enhanced with improved cytotoxicity and resistance to immunosuppression imposed by tumor microenvironments. Certain aspects include modified T cells and pharmaceutical compositions comprising the modified cells for adoptive cell therapy and treating a disease or condition associated with enhanced immunity.

8 Claims, 26 Drawing Sheets

Specification includes a Sequence Listing.

(56) References Cited

U.S. PATENT DOCUMENTS

| | | | |
|---|---|---|---|
| 6,120,766 | A | 9/2000 | Hale et al. |
| 6,905,681 | B1 | 6/2005 | June et al. |
| 2005/0042664 | A1 | 2/2005 | Wu et al. |
| 2005/0079184 | A1 | 4/2005 | Hsing-Chang et al. |
| 2006/0025576 | A1 | 2/2006 | Miller et al. |
| 2007/0110742 | A1 | 5/2007 | Chae et al. |
| 2009/0202501 | A1 | 8/2009 | Zhang |
| 2013/0315884 | A1 | 11/2013 | Galetto |
| 2014/0099309 | A1 | 4/2014 | Powell et al. |
| 2014/0227272 | A1* | 8/2014 | Kufer ............... C07K 16/18 514/706 |
| 2014/0271687 | A1 | 9/2014 | Kovesdi et al. |
| 2015/0140019 | A1 | 5/2015 | June et al. |
| 2015/0175711 | A1 | 6/2015 | Leung |
| 2015/0322169 | A1* | 11/2015 | June ............... C07K 16/2803 424/278.1 |
| 2016/0022829 | A1* | 1/2016 | Yurkovetskiy ..... A61K 39/3955 424/78.3 |
| 2016/0272999 | A1* | 9/2016 | Duchateau ............... A61P 35/00 |
| 2017/0335281 | A1* | 11/2017 | Loew ............ A61K 39/001164 |

FOREIGN PATENT DOCUMENTS

| | | | |
|---|---|---|---|
| CN | 104136458 A | | 11/2014 |
| CN | 104583230 A | | 4/2015 |
| CN | 104718284 A | | 6/2015 |
| EP | 239400 A2 | | 9/1987 |
| WO | 9109967 A1 | | 7/1991 |
| WO | 9201472 A1 | | 2/1992 |
| WO | 9308829 A1 | | 5/1993 |
| WO | 2009089004 A1 | | 7/2009 |
| WO | 2011057124 A1 | | 5/2011 |
| WO | 2014011988 A2 | | 1/2014 |
| WO | 2014011988 A3 | | 3/2014 |
| WO | 2014151960 A2 | | 9/2014 |
| WO | 2015090230 A1 | | 6/2015 |
| WO | 2015112626 A1 | | 7/2015 |
| WO | 2015123527 A1 | | 8/2015 |
| WO | 2016070061 A1 | | 5/2016 |
| WO | WO 2016087245 | * | 6/2016 |

OTHER PUBLICATIONS

Kim et al., Redirection of Genetically Engineered CAR-T Cells Using Bifunctional Small Molecules, J. Am. Chem. Soc. 2015, 137, 2832-2835.*

Junttila et al., Antitumor Efficacy of a Bispecific Antibody That Targets HER2 and Activates T Cells, Cancer Res; 74(19); 2014, 5561-71.*

Shyer et al., Metabolic signaling in T cells, Cell Research (2020) 30:649-659.*

Baca, et al.,Antibody Humanization Using Monovalent Phage Display, 1997, J Biol Chem, 272(16):10678-10684.

Bird, et al.,Single-chain Antigen-Binding Proteins, 1988, Science 242:423-426.

Brennan, et al.,Preparating of bispecific antibodies by chemical recombination of monoclonal immunoglobulin G1 fragments., Science 229:81-3 (1985) Abstract.

Bruggerman, et al.,Designer Mice: The Production of Human Antibody Repertoires in Transgenic Animals, 1993, Year in Immunol 7:33-40.

Caldas, et al.,Design and synthesis of germline-based hemi-humanized single-chain Fv against the CD18 surface antigen, Protein Eng., 13(5):353-60 (2000).

Carter, et al.,Humanization of an anti-p185HER2 antibody for human cancer therapy., Proc. Natl. Acad. Sci. USA, 89:4285-89 (1992).

Chothia, et al.,Canonical structures for the hypervariable regions of immunoglobulins., J Mol Biol. Aug. 20, 1987;196(4):901-17. (Abstract).

Couto, et al.,Anti-BA46 Monoclonal Antibody Mc3: Humanization Using a Novel Positional Consensus and in Vivo and in Vitro Characterization., Cancer Res., 55(8):1717-22 (1995).

Couto, et al., Designing Human Consensus Antibodies with Minimal Positional Templates, Cancer Res., 55 (23 Supp):5973s-5977s (1995).

Duchosal, et al.,Immunization of hu-PBL-SCID mice and the rescue of human monoclonal Fab fragments through combinatorial libraries., 1992, Nature 355:258-262.

Gall, et al.,T cells armed with anti-CD3 x anti-CD20 bispecific antibody enhance killing of CD20+ malignant B cells and bypass complement-mediated rituximab resistance in vitro., Experimental Hematology 2005, 33:452-459—Abstract.

Grabert, et al., "Human TCells Armed with Her2/neu Bispecific Antibodies Divide, Are Cytotoxic, and Secrete Cytokines with Repeated Stimulation.", Clin. Canc. Res., 12:569-576, 2006.

Gruber, et al.,""Efficient tumor cell lysis mediated by a bispecific single chain antibody expressed in *Escherichia coli.*, J. Immunol., 152:5368-74 (1994) (abstract).

Hollinger, et al.,'Diabodies': Small bivalent and bispecific antibody fragments., Proc. Natl. Acad. Sci. USA, 90:6444-6448 (1993).

Hoogenboom, et al., By-passing immunisation. Human antibodies from synthetic repertoires of germline VH gene segments arranged in vitro., J Mol Biol Sep. 20, 1992;227(2):381-8. (Abstract).

Huston, et al.,"Protein engineering of antibody binding sites: Recovery of specific activity in an anti-digoxin single-chain Fv analogue produced in *Escherichia coli.*", 1988, Proc. Natl. Acad. Sci. USA 85:5879-5883.

Jakobovits, et al.,Analysis of homozygous mutant chimeric mice: Deletion of the immunoglobulin heavy-chain joining region blocks B-cell development and antibody production, Proc. Natl. Acad. Sci. 90 ,1993 ,2551-2555.

Jakobovits, et al.,Germ-line transmission and expression of a human-derived yeast artificial chromosome, Nature, 362:255-258 (1993).

Jones, et al.,Replacing the complementarity-determining regions in a human antibody with those from a mouse, Nature, 321:522-525 (1986).

Kostelny, et al.,"Formation of a bispecific antibody by the use of leucine zippers, Formation of a bispecific antibody by the use of leucine zippers," J. Immunol., vol. 148, No. 5, pp. 1547-1553 (1992) , 1992 ,1547-1553.

Onberg, et al.,Human antibodies from transgenic mice., Int. Rev. Immunol., 13:65-93 (1995).

Marks, et al.,By-passing immunization. Human antibodies from V-gene libraries displayed on phage, J. Mol. Biol. 222:581-597 (1991).

McCafferty, et al.,Phage antibodies: filamentous phage displaying antibody variable domains, Nature, 348:552-553 (1990)93).

Milstein, et al.,Hybrid hybridomas and their use in immunohistochemistry, (1983) Nature 305: 537-39. (abstract).

Morea, et al.,Antibody modeling: implications for engineering and design, Methods, 20(3):267-79 (2000).

Padlan, et al.,A possible procedure for reducing the immunogenicity of antibody variable domains while preserving their ligand-binding properties, 1991, Molecular Immunology, 28(4/5):489-498.

Pedersen, et al.,Comparison of surface accessible residues in human and murine immunoglobulin Fv domains. Implication for humanization of murine antibodies., J. Mol. Biol., 235(3):959-73 (1994).

Presta, et al.,Antibody engineering, Current Opinion in Biotechnology 3 , 1992 ,394-398.

Presta, et al.,Humanization of an antibody directed against IgE, J. Immunol., 151:2623-32 (1993).

Riechmann, et al.,Reshaping human antibodies for therapy, Nature, 332:323-327 (1988).

Roder, et al.,The EBV-hybridoma technique, Methods Enzymol., 121:140-167 (1986).

Roguska, et al.,A comparison of two murine monoclonal antibodies humanized by CDR-grafting and variable domain resurfacing, Protein Eng., 9(10):895-904 (1996).

Roguska, et al.,Humanization of murine monoclonal antibodies through variable domain resurfacing, PNAS, 91:969-973 (1994).

Rosenberg, et al.,Use of Tumor-Infiltrating Lymphocytes and Interleukin-2 in the Immunotherapy of Patients with Metastatic Melanoma, New Eng. J. of Med. 319:1676-1680, 1988.

Sandhu, et al.,A rapid procedure for the humanization of monoclonal antibodies., Gene, 150(2):409-10(1994).

(56) References Cited

OTHER PUBLICATIONS

Sen, et al., "Use of Anti-CD3 x Anti-HER2/neu Bispecific Antibody for Redirecting Cytotoxicity of Activated T Cells toward HER2/neu+ Tumors.", Journal of Hematotherapy and Stem Cell Research 2001, 10:247-260.

Sims, et al., A humanized CD18 antibody can block function without cell destruction, J. Immunol., 151:2296-2308 (1993).

Skerra, et al., Assembly of a Functional Immunoglobulin Fv Fragment in *Escherichia coli*, Science, 240, 1988, 1038-1041.

Studnicka, et al., Human-engineered monoclonal antibodies retain full specific binding activity by preserving non-CDR complementarity-modulating residues, Protein Engineering, 7(6):805-814 (1994).

Tan, et al.,"" 'Superhumanized' antibodies: reduction of immunogenic potential by complementarity-determining region grafting with human germline sequences: application to an anti-CD28, J. Immunol., 169:1119-25 (2002).

Thakur, et al., Microenvironment generated during EGFR targeted killing of pancreatic tumor cells by ATC inhibits myeloid-derived suppressor cells through COX2 and PGE2 dependent pathway., Journal of Translational Medicine 2013, 11:35 (10 pages).

Traunecker, et al., Bispecific single chain molecules (Janusins) target cytotoxic lymphocytes on HIV infected cells, Embo J. 10: 3655-9 (1991).

Tutt, et al., Trispecific F(ab')3 derivatives that use cooperative signaling via the TCR/CD3 complex and CD2 to activate and redirect resting cytotoxic T cells, J. Immunol. 147: 60-9 (1991) (abstract).

Urbanska, et al., "Targeted cancer immunotherapy via combination of designer bispecific antibody and novel gene-engineered T cells.", J Transl Med. 2014; 12: 347. (12 pages).

Vaughan, et al., Human antibodies with sub-nanomolar affinities isolated from a large non-immunized phage display library., Vaughan et al., 1996, Nature Biotech., 14:309-14 (Abstract).

Verhoeyen, et al., Reshaping human antibodies: grafting an antilysozyme activity, Science, 239:1534-1536 (1988).

Ward, et al., "Binding activities of a repertoire of single immunoglobulin variable domains secreted from *Escherichia coli*." Nature 341:544-546 (1989).

Wu, et al., Humanization of a murine monoclonal antibody by simultaneous optimization of framework and CDR residues., J. Mol. Biol., 294:151-162 (1999).

Spear et al. NKG2D Ligands As Therapeutic Targets. Cancer Immunity, 2013. 13: p. 8; 14 pages.

Sharon et al. Recombinant Polyclonal Antibodies for Cancer Therapy. Journal Cellular Biochemistry, 2005. 96:305-313.

Müller and Kontermann. Bispecific Antibodies for Cancer Immunotherapy. Biodrugs, 2010. 24(2): 89-98.

Long et al. 4-1BB Costimulation Ameliorates T Cell Exhaustion Induced By Tonic Signaling of Chimeric Antigen Receptors. Nature Medicine, Jun. 2015. 21(6): 581-593.

Shirasu et al., "Functional Design of Chimeric T-Cell Antigen Receptors for Adoptive Immunotherapy of Cancer: Architecture and Outcomes," AntiCancer Res. 32: 2377-2384 (2012).

\* cited by examiner

MALPVTALLLPLALLLHAARPGSTTTPAPRPP
TPAPTIASQPLSLRPEACRPAAGGAVHTRGLD
FACDIYIWAPLAGTCGVLLLSLVITLYCSAKR
GRKKLLYIFKQPFMRPVQTTQEEDGCSCRFPE
EEEGGCELRVKFSRSADAPAYKQGQNQLYNEL
NLGRREEYDVLDKRRGRDPEMGGKPRRKNPQE
GLYNELQKDKMAEAYSEIGMKGERRRGKGHDG
LYQGLSTATKDTYDALHMQALPPR (SEQ ID NO: 1)

SEQUENCE LISTING

```
<160> NUMBER OF SEQ ID NOS: 1

<210> SEQ ID NO 1
<211> LENGTH: 248
<212> TYPE: PRT
<213> ORGANISM: Artificial Sequence
<220> FEATURE:
<223> OTHER INFORMATION: Artificially generated

<400> SEQUENCE: 1

Met Ala Leu Pro Val Thr Ala Leu Leu Leu Pro Leu Ala Leu Leu Leu
1               5                   10                  15

His Ala Ala Arg Pro Gly Ser Thr Thr Thr Pro Ala Pro Arg Pro Pro
            20                  25                  30

Thr Pro Ala Pro Thr Ile Ala Ser Gln Pro Leu Ser Leu Arg Pro Glu
        35                  40                  45
```

-continued

```
Ala Cys Arg Pro Ala Ala Gly Gly Ala Val His Thr Arg Gly Leu Asp
     50                  55                  60
Phe Ala Cys Asp Ile Tyr Ile Trp Ala Pro Leu Ala Gly Thr Cys Gly
 65              70                  75                  80
Val Leu Leu Leu Ser Leu Val Ile Thr Leu Tyr Cys Ser Ala Lys Arg
                 85                  90                  95
Gly Arg Lys Lys Leu Leu Tyr Ile Phe Lys Gln Pro Phe Met Arg Pro
             100                 105                 110
Val Gln Thr Thr Gln Glu Glu Asp Gly Cys Ser Cys Arg Phe Pro Glu
         115                 120                 125
Glu Glu Glu Gly Gly Cys Glu Leu Arg Val Lys Phe Ser Arg Ser Ala
         130                 135                 140
Asp Ala Pro Ala Tyr Lys Gln Gly Gln Asn Gln Leu Tyr Asn Glu Leu
145                 150                 155                 160
Asn Leu Gly Arg Arg Glu Glu Tyr Asp Val Leu Asp Lys Arg Arg Gly
             165                 170                 175
Arg Asp Pro Glu Met Gly Gly Lys Pro Arg Arg Lys Asn Pro Gln Glu
             180                 185                 190
Gly Leu Tyr Asn Glu Leu Gln Lys Asp Lys Met Ala Glu Ala Tyr Ser
         195                 200                 205
Glu Ile Gly Met Lys Gly Glu Arg Arg Arg Gly Lys Gly His Asp Gly
     210                 215                 220
Leu Tyr Gln Gly Leu Ser Thr Ala Thr Lys Asp Thr Tyr Asp Ala Leu
225                 230                 235                 240
His Met Gln Ala Leu Pro Pro Arg
             245
```

METHODS AND COMPOSITIONS FOR CELLS EXPRESSING A CHIMERIC INTRACELLULAR SIGNALING MOLECULE

CROSS-REFERENCE TO RELATED APPLICATIONS

The present application is a is a 35 U.S.C. § 371 national phase application from, and claims priority to, International Application No. PCT/US2016/049087 filed Aug. 26, 2016, which claims priority under 35 U.S.C. § 119(e) to U.S. Provisional Patent Application No. 62/211,311, filed Aug. 28, 2015, which is incorporated herein by reference in its entirety.

STATEMENT REGARDING FEDERALLY SPONSORED RESEARCH OR DEVELOPMENT

This invention was made with government support under CA120409-07 awarded by the National Institutes of Health. The government has certain rights in the invention.

BACKGROUND OF THE INVENTION

During growth of a tumor, the tumor rapidly outgrows its blood supply, leaving portions of the tumor with regions where the oxygen concentration is significantly lower than in healthy tissues. Hypoxic microenvironements in solid tumors are the result of the consummation of available oxygen by rapidly proliferating tumor cells, thus limiting the amount of oxygen available to diffuse further into the tumor tissue. In order to support continuous growth and proliferation in challenging hypoxic environments, cancer cells have developed mechanisms to alter their metabolism. Thus, hypoxia is associated with increased tumor resistance to chemotherapy and radiation treatment.

Many conventional reactive chemotherapies are not able to penetrate into hypoxic zones that are located at a distance from the blood vessels. Moreover, chronic hypoxia limits cancer cell proliferation, rendering the quiescent tumor cells in the hypoxic region of the tumor less susceptible to conventional antiproliferative agents, which typically target actively dividing cells in close proximity to the blood vessels. Under conditions of cell hypoxia, genomic instability can lead to tumor cell variants that can survive in an oxygen depleted environment through clonal selection and expansion. This clonal expansion can lead to tumor progression, metastasis, acquired resistance to chemotherapy, and treatment failure that compromise clinical outcomes.

Given the role hypoxia plays in tumor progression, metastasis, and resistance to therapy, and ultimately treatment failure, a need exists for more effective methods to combat cancer cells that are resistant to therapy. The present invention satisfies this need.

SUMMARY OF THE INVENTION

As described herein, the present invention relates to compositions, methods, and uses for metabolically enhanced tumor specific T cells. One aspect of the invention includes a method of metabolically enhancing a tumor specific T cell. The method comprises introducing a chimeric antigen receptor (CAR) into a T cell. The CAR comprises an antigen binding domain, a transmembrane domain and an intracellular domain of a co-stimulatory molecule. The CAR T cell is armed with a bispecific antibody and the bispecific antibody binds to a target on a tumor cell and the CAR T cell. At least one co-stimulatory molecule on the armed CAR T cell is stimulated. Stimulation activates the intracellular domain of the co-stimulatory molecule thereby metabolically enhancing the tumor specific T cell.

In another aspect, the invention provides a metabolically enhanced, tumor specific T cell comprising a chimeric antigen receptor (CAR) and a bispecific antibody. The CAR comprises an antigen binding domain, a transmembrane domain and an intracellular domain of a co-stimulatory molecule. The bispecific antibody binds to a target on a tumor cell and the T cell, and the T cell has improved cytotoxicity and resistance to immunosuppression at a solid tumor site.

In various embodiments of the above aspects or any other aspect of the invention delineated herein, introducing the CAR into the T cell comprises introducing a nucleic acid sequence encoding the CAR. In another embodiment, introducing the nucleic acid sequence comprises electroporating an mRNA encoding the CAR.

In other embodiments, arming the CAR T cell comprises contacting the CAR T cell with the bispecific antibody. In another embodiment, arming the CAR T cell comprises introducing a nucleic acid sequence encoding the bispecific antibody. In yet another embodiment, arming the CAR T cell comprises arming the CAR T cell with two or more bispecific antibodies, wherein the CAR T cell displays the two or more bispecific antibodies. In still another embodiment, the two or more bispecific antibodies specifically bind the CAR T cell. In another embodiment, the bispecific antibodies comprise a combination of antibodies selected from the group consisting of anti-CD3, anti-IgD Fc, and anti-IgA Fc. In certain embodiments, the bispecific antibody is chemically heteroconjugated to a polyclonal antibody specific for a tumor-associated antigen (TAA), wherein the T cells specifically bind the TAA polyclonal antibody. In other embodiments, introducing the nucleic acid sequence comprises electroporating an mRNA encoding the bispecific antibody.

In certain embodiments, stimulating the armed CAR T cell improves cytotoxicity and resistance to immunosuppression of the armed CAR T cell when in a tumor microenvironment. Certain embodiments further comprise irradiating the CAR T cell with up to 2500 rad, wherein said irradiation is sufficient to inhibit proliferation of the CAR T cell but is insufficient to inhibit cytokine secretion or cytotoxicity.

Another embodiment includes a composition comprising the metabolically enhanced tumor specific T cell generated according to the methods of the present invention. Yet another embodiment includes a pharmaceutical composition comprising the metabolically enhanced, tumor specific T cell of the present invention and a pharmaceutically acceptable carrier.

In another embodiment, the T cell of the present invention comprises a nucleic acid sequence encoding the CAR. In other embodiments, the T cell comprises a nucleic acid sequence encoding the bispecific antibody.

Another embodiment includes use of the T cell of the present invention in the manufacture of a medicament for the treatment of a tumor or cancer in a subject in need thereof. Yet another embodiment includes a method of treating a disease or condition associated with a tumor or cancer in a subject comprising administering to the subject a therapeutically effective amount of a pharmaceutical composition comprising the T cell of the present invention. Another embodiment includes a method of treating a solid tumor in a subject, comprising administering to the subject a therapeutically effective amount of a pharmaceutical composition comprising the T cell of the present invention. Still another embodiment includes a method for stimulating a T cell-mediated immune response to a target tumor cell or tumor tissue in a subject comprising administering to a subject a therapeutically effective amount of a pharmaceutical composition comprising the T cell of the present invention.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Definitions

Figure 1:
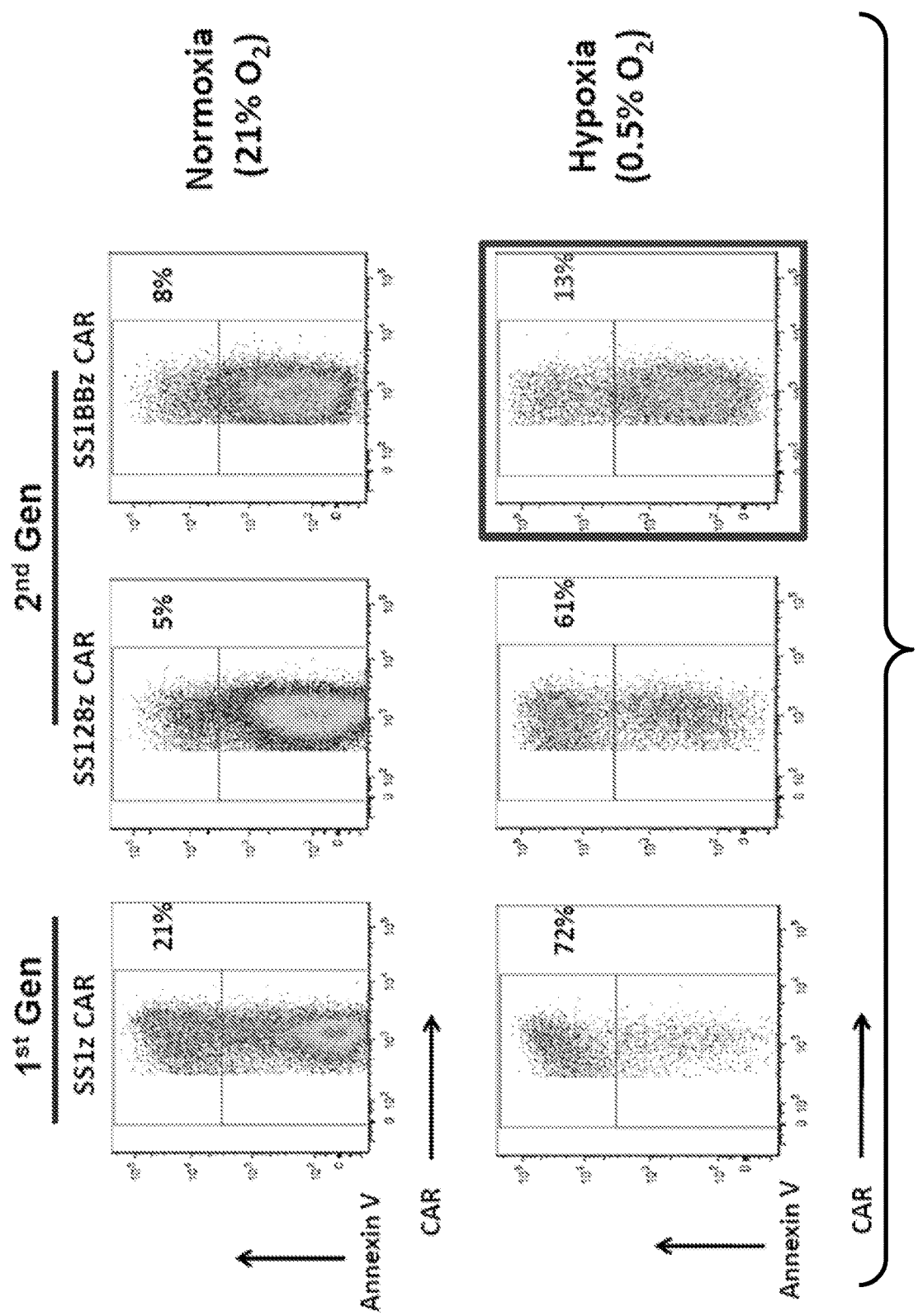
FIG. 1 is a panel of graphs showing hypoxia differentially affected CAR T cell survival depending on the co-stimulatory endodomain.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

A "bispecific antibody," as used herein, refers to an antibody having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan et al. (1985) Science 229:81. Bispecific antibodies include bispecific antibody fragments. See, e.g., Holliger et al. (1993) Proc. Natl. Acad. Sci. U.S.A. 90:6444-48, Gruber et al. (1994) J. Immunol. 152:5368.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "arming" as used herein refers to displaying the bispecific antibody on the surface of the cell. In one embodiment, the bispecific antibody specifically binds to an antigenic epitope on the cell to be armed with the bispecific antibody, such as a T cell, and binds another antigenic epitope, such as an antigenic epitope on a target cell, such as another cell.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

"Bispecificity," as used herein, refers to a molecule having binding specificities for at least two different binding epitopes. In one embodiment, the epitopes are from the same binding partner. In another embodiment, the epitopes are from two different binding partners. The molecule with bispecificity to different epitopes may include a bispecific antibody.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to CD3-zeta transmembrane and intracellular domain. The specificity of CAR designs may be derived from ligands of receptors (e.g., peptides). In some embodiments, a CAR can target cancers by redirecting the specificity of a T cell expressing the CAR specific for tumor associated antigens.

The term "chimeric intracellular signaling molecule" refers to recombinant receptor comprising one or more intracellular domains of one or more co-stimulatory molecules. The chimeric intracellular signaling molecule substantially lacks an extracellular ligand-binding domain, such as an non-antigen binding domain, or substantially lacks an extracellular domain. In some embodiments, the chimeric intracellular signaling molecule comprises additional domains, such as a transmembrane domain, a detectable tag, and a spacer domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

A "co-stimulatory signal", as used herein, refers to a signal, which in combination with a primary signal, such as TCR/CD3 ligation, leads to T cell proliferation and/or upregulation or downregulation of key molecules.

The term "cytotoxic" or "cytotoxicity" refers to killing or damaging cells. In one embodiment, cytotoxicity of the metabolically enhanced cells is improved, e.g. increased cytolytic activity of T cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. As applied to the nucleic acid or protein, "homologous" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The guide nucleic acid sequence may be complementary to one strand (nucleotide sequence) of a double stranded DNA target site. The percentage of complementation between the guide nucleic acid sequence and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The guide nucleic acid sequence can be at least 10, 11, 12, 13, 14, 15, 16, 17, 18, 19, 20, 21, 22, 23, 24, 25, 26, 27, 28, 29, 30, 31, 32, 33, 34, 35 or more nucleotides in length. In some embodiments, the guide nucleic acid sequence comprises a contiguous stretch of 10 to 40 nucleotides. The variable targeting domain can be composed of a DNA sequence, a RNA sequence, a modified DNA sequence, a modified RNA sequence (see for example modifications described herein), or any combination thereof.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "ligand" refers to a molecule, compound, or other binding partner that has a binding site with binding specificity for a ligand-binding domain. A ligand can also be referred to as a "antigen."

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "resistance to immunosuppression" refers to lack of suppression or reduced suppression of an immune system activity or activation.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the term "substantially lacks an extracellular domain" refers to a molecule that is essentially free of a domain that extrudes extracellularly. In one embodiment, the chimeric intracellular signaling molecule lacks any function performed by an extracellular domain, such as antigen binding. In another embodiment, the chimeric intracellular signaling molecule includes a transmembrane domain but lacks a functional extracellular domain.

As used herein, the term "substantially lacks an extracellular ligand-binding domain" refers to a molecule that is essentially free of a binding domain that specifically binds to a molecule. In one embodiment, the chimeric intracellular signaling molecule lacks any functional ligand-binding domain in the extracellular domain, such as lacking an antigen binding domain. In another embodiment, the chimeric intracellular signaling molecule includes an extracellular domain but lacks the capacity to specifically bind to a ligand, such as an antigen.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The term "tumor" as used herein, refers to an abnormal growth of tissue that may be benign, pre-cancerous, malignant, or metastatic.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention includes methods of and compositions for enhancing T cell metabolism and activity in order to provide T cells that are more effective for adoptive T cell therapy. According to the invention, T cells are metabolically enhanced and have improved cytotoxicity and resistance to immunosuppression imposed by tumor microenvironments when they express a chimeric intracellular signaling molecule or a chimeric antigen receptor.

The invention also includes a combination approach for adoptive cell therapy by arming the metabolically enhanced T cells with bispecific antibodies (BiAb). The presence of T regulatory cells (CD4+/CD25$^{hi}$/CD127$^{lo}$), granulocytic (CD14$^-$/HLA-DR$^-$/CD11b$^+$/CD33$^+$) and monocytic (CD14$^+$/HLA-DR$^-$/CD11b$^+$/CD33$^+$) myeloid derived suppressor cell (MDSC) populations modify the tumor microenvironment to sabotage the ability of incoming immune effector cells. In vitro models have shown that T cells armed with bispecific antibodies inhibit MDSC differentiation and attenuate T regulatory and MDSC suppressor activity (Thakur A, et al., J Transl Med., 11:35, 2013). Arming T cells with bispecific antibodies also induced the cells to secrete Th1 cytokines, kill target cells, and expand after tumor engagement to shift the tumor microenvironment to a Th1 environment (Grabert, R. C., et al., Clin. Canc. Res., 12:569-576, 2006) and vaccinate the patient with their own tumor antigens.

Based on observations of these modified T cells, a new modality of T cell therapy has been developed and is described herein using metabolically enhanced T cells alone or metabolically enhanced T cells that also encode a BiAb to improve treatment efficacy.

Chimeric Intracellular Signaling Molecule

The present invention includes a chimeric intracellular signaling molecule within a T cell. In one aspect, the invention includes a modified T cell comprising an isolated nucleic acid sequence encoding a chimeric intracellular signaling molecule, wherein the isolated nucleic acid sequence comprises a nucleic acid sequence of an intracellular domain of a co-stimulatory molecule and substantially lacks an extracellular ligand-binding domain, wherein the T cell expresses the chimeric intracellular signaling molecule.

In another aspect, the invention includes a modified T cell comprising a chimeric intracellular signaling molecule, wherein the chimeric intracellular signaling molecule comprises an intracellular domain of a co-stimulatory molecule and substantially lacks an extracellular ligand-binding domain.

In yet another aspect, the invention includes a population of cells comprising a nucleic acid encoding a chimeric intracellular signaling molecule comprising an intracellular domain and substantially lacks an extracellular ligand-binding domain, wherein the population of cells express the chimeric intracellular signaling molecule.

In one embodiment, the chimeric intracellular signaling molecule lacks any functional ligand-binding domain in the extracellular domain, such as lacking an antigen binding domain. In another embodiment, the chimeric intracellular signaling molecule includes an extracellular domain, but lacks the capacity to specifically bind to a ligand or molecule. In yet another embodiment, the chimeric intracellular signaling molecule substantially lacks an extracellular domain.

In another aspect, the invention includes a metabolically enhanced T cell comprising a chimeric intracellular signaling molecule comprising an intracellular domain of a co-stimulatory molecule and an extracellular domain comprising a non-antigen binding domain of an antibody, such as a single chain fragment comprising the non-antigen binding portion and lacking the variable region or a Fc portion of an antibody, i.e., IgD or IgA.

In yet another aspect, the invention includes a metabolically enhanced T cell comprising a chimeric intracellular signaling molecule comprising an intracellular domain of a co-stimulatory molecule, and substantially lacks an extracellular ligand-binding domain. The metabolically enhanced T cell expresses the chimeric intracellular signaling molecule. In certain embodiments, expression of the chimeric intracellular signaling molecule metabolically enhances the T cell. In some embodiments, expression of the chimeric intracellular signaling molecule improves cytotoxicity and resistance to immunosuppression when in a tumor microenvironment.

Intracellular Domain

The intracellular domain or otherwise the cytoplasmic domain of the chimeric intracellular signaling molecule of the invention, is responsible for activation of the cell in which the chimeric intracellular signaling molecule is expressed. The term "intracellular domain" is thus meant to include any truncated portion of the intracellular domain sufficient to transduce the activation signal. In one embodiment, the intracellular domain includes a domain responsible for an effector function. The term "effector function" refers to a specialized function of a cell. Effector function of a T cell, for example, may be cytolytic activity or helper activity including the secretion of cytokines.

In one embodiment, the intracellular domain includes a domain responsible for signal activation and/or transduction. The intracellular domain may transmit signal activation via protein-protein interactions, biochemical changes or other response to alter the cell's metabolism, shape, gene expression, or other cellular response to activation of the chimeric intracellular signaling molecule.

In one embodiment, a cell comprising a chimeric intracellular signaling molecule is metabolically enhanced. In another embodiment, a cell comprising a chimeric intracellular signaling molecule has improved cytotoxicity and resistance to immunosuppression, such as when the cell is in a tumor microenvironment.

Examples of an intracellular domain for use in the invention include, but are not limited to, the cytoplasmic portion of the T cell receptor (TCR) and any co-stimulatory molecule that acts in concert to initiate signal transduction following antigen receptor engagement, as well as any derivative or variant of these elements and any synthetic sequence that has the same functional capability.

Examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

In one embodiment, the intracellular domain of the chimeric intracellular signaling molecule includes any portion of a co-stimulatory molecule, such as at least one signaling domain from CD3, CD27, CD28, ICOS, 4-1BB, PD-1, T cell receptor (TCR), co-stimulatory molecules, any derivative or variant of these sequences, any synthetic sequence that has the same functional capability, and any combination thereof.

Other Domains of the Chimeric Intracellular Signaling Molecule

The chimeric intracellular signaling molecule may include a detectable tag. As used herein, the term "protein tag" or "detectable tag" or "tag" generally means any oligo- or polypeptide that is connected to the chimeric intracellular signaling molecule to detect the chimeric intracellular signaling molecule. The tag may be attached to the intracellular domain, a hinge domain, a transmembrane domain or other domain of the chimeric intracellular signaling molecule. The tag may include up to 100 amino acids, between 10 to 50 amino acids, or between 5 to 25 amino acids. The tag may be removed or cleaved from the chimeric intracellular signaling molecule by a chemical agent or enzyme, such as protease, intein splicing, peptidase, etc. The tag may also be used for affinity purification of the chimeric intracellular signaling molecule. Examples of a tag includes, but is not limited to, chitin binding protein, maltose binding protein, thioredoxin-tag, fluorescent tag, glutathione-S-transferase (GST), poly(His) tag, V5-tag, Myc-tag, HA-tag, biotin or biotin-like molecules, streptavidin binding molecules, FLAG tag, or other tags known in the art.

The chimeric intracellular signaling molecule may include a spacer domain. As used herein, the term "spacer domain" generally means any oligo- or polypeptide that functions to link any domains, such as linking the transmembrane domain to, either the extracellular domain or, the cytoplasmic domain in the polypeptide chain. A spacer domain may be on one or both ends of the chimeric intracellular signaling molecule. A spacer domain may comprise up to 300 amino acids, preferably 10 to 100 amino acids and most preferably 25 to 50 amino acids.

In some embodiments, the chimeric intracellular signaling molecule further comprises a hinge and/or transmembrane domain. In one embodiment, the chimeric intracellular signaling molecule further comprises a hinge and/or transmembrane domain, such as a CD28 transmembrane domain and a CD8-alpha hinge domain. Examples of the hinge and/or transmembrane domain include, but are not limited to, a hinge and/or transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIR, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, NKG2C, and any combination thereof.

Bispecific Antibody

The present invention also encompasses a bispecific antibody. In one embodiment, the metabolically enhanced cell of the invention further comprises a bispecific antibody. The bispecific antibody comprises two different binding specificities and thus binds to two different antigens. In such an embodiment, the bispecific antibody comprises a first antigen binding domain that binds to a first antigen and a second antigen binding domain that binds to a second antigen. The bispecific antibody may specifically bind to more than one epitope on the same target, such as a cell or receptor, or to more than one epitope on different targets. In another embodiment, the bispecific antibody comprises a bispecific antigen binding domain.

The present invention should not be construed to be limited to any particular bispecific antibody. Rather, any bispecific antibody is useful in the present invention. The bispecific antibody may be constructed from a synthetic antibody, a human antibody, a humanized antibody, a single chain variable fragment (scFv), a single domain antibody, an antigen binding fragment thereof, and any combination thereof. In one embodiment, the bispecific antibody is constructed by linking two different antibodies, or portions thereof, such as Fab, F(ab')$_2$, Fab', scFv, and sdAb from two different antibodies. Techniques for making human and humanized antibodies and antibody fragments, such as a scFv, are also described elsewhere herein. In another embodiment, the bispecific antibody comprises an antigen binding domain comprising a first and a second single chain variable fragment (scFv) molecule.

Techniques for engineering and expressing bispecific antibodies include, but are not limited to, recombinant co-expression of two immunoglobulin heavy chain-light chain pairs having different specificities (see Milstein and Cuello, Nature 305: 537 (1983), WO 93/08829, and Traunecker et al., EMBO J. 10: 3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science 229:81 (1985)); using leucine zippers to produce bispecific antibodies (see, e.g., Kostelny et al., J. Immunol. 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991). Engineered antibodies with three or more functional antigen binding sites, including "Octopus antibodies," are also included herein (see, e.g. US 2006/0025576A1).

The present invention includes a bispecific antibody having an antigen binding domain that binds to a target cell. In one embodiment, the bispecific antibody has specificity for a target cell antigen. In another embodiment, the bispecific antibody comprises an antibody or fragment thereof that specifically binds to the target cell antigen. The target cell antigen may include the same target cell antigen that the T cell receptor binds to or may include a different target cell antigen. The target cell antigen may include any type of ligand found on the surface of a target cell including ligands on T cells (e.g. CD3, CD2, or other antigens expressed on T cell blasts). For example, the target cell antigen may be chosen because it recognizes a ligand that acts as a cell marker on a target cell that is associated with a particular disease state. Thus examples of cell markers that may act as ligands for the antigen moiety domain in a bispecific antibody include those associated with viral, bacterial and parasitic infections, autoimmune disease and cancer cells. In one embodiment, the target cell antigen includes any tumor associated antigen (TAA), any viral antigen, or any fragment thereof.

In another embodiment, the bispecific antibody has specificity for at least one antigen on a T cell, such as the metabolically enhanced T cell as described elsewhere herein. The T cell antigen includes an antigen found on the surface of a T cell. The T cell antigen may include a co-stimulatory molecule as described elsewhere herein. In one embodiment, the T cell antigen is CD3, CD4, CD8, T cell receptor (TCR), or any fragment thereof. In this embodiment, the bispecific antibody comprises an antibody that specifically binds to the T cell antigen. Examples of the bispecific antibody may include anti-CD3, anti-CD4, anti-CD8, anti-TCR, anti-IgD Fc, anti-IgA Fc, any fragment thereof, and any combination thereof. The other target antigen of the bispecific antibody could also be a T cell antigen such as CD3, CD4, CD8, TCR, or any fragment thereof (e.g. anti-CD3×anti-CD3 construct). In another embodiment, the bispecific antibody is chemically heteroconjugated to a polyclonal antibody specific for a tumor-associated antigen (TAA), and the T cell specifically binds the TAA polyclonal antibody.

Another embodiment of the invention includes the metabolically enhanced T cell described herein wherein the first antigen binding domain binds to a target cell and a second antigen binding domain binds to an activated T cell.

The metabolically enhanced T cell described elsewhere herein may be armed with the bispecific antibody. When a cell is armed with the bispecific antibody, the cell is contacted with bispecific antibody and the bispecific antibody specifically binds to an antigen on the surface of the cell through one antigen binding domain of the bispecific antibody. In another embodiment, the T cell is armed with two or more bispecific antibodies and the T cell displays the two or more bispecific antibodies. In such an embodiment, the T cell specifically binds to at least two of the bispecific antibodies.

Alternatively, the bispecific antibody may be expressed and secreted by the cell. When the cell expresses the bispecific antibody, a nucleic acid sequence encoding the bispecific antibody may be introduced into the cell. The nucleic acid sequence may be introduced by any method described elsewhere herein or other methods known in the art. In one embodiment, the cell is electroporated with a nucleic acid sequence encoding the bispecific antibody.

Chimeric Antigen Receptor (CAR)

In another aspect of the invention, the metabolically enhanced T cell is generated by expressing a CAR therein. Thus, the present invention encompasses a CAR and a nucleic acid construct encoding a CAR, wherein the CAR includes an antigen binding domain, a transmembrane domain and an intracellular domain.

One or more domains or a fragment of a domain of the CAR may be human. In one embodiment, the present invention includes a fully human CAR. The nucleic acid sequences coding for the desired domains can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as a cloned molecule.

In one aspect, the invention includes a metabolically enhanced, tumor specific T cell comprising a chimeric antigen receptor (CAR) and a bispecific antibody, wherein the CAR comprises an antigen binding domain, a transmembrane domain and an intracellular domain of a co-stimulatory molecule, and the bispecific antibody binds to a target on a tumor cell and the T cell, and wherein the T cell has improved cytotoxicity and resistance to immunosuppression at a solid tumor site. In one embodiment, the T cell comprises a nucleic acid sequence encoding the CAR and, optionally, a nucleic acid sequence encoding the bispecific antibody.

Antigen Binding Domain

In one embodiment, the CAR of the invention comprises an antigen binding domain that binds to an antigen on a target cell. Examples of cell surface markers that may act as an antigen that binds to the antigen binding domain of the CAR include those associated with viral, bacterial and parasitic infections, autoimmune disease, and cancer cells.

The choice of antigen binding domain depends upon the type and number of antigens that are present on the surface of a target cell. For example, the antigen binding domain may be chosen to recognize an antigen that acts as a cell surface marker on a target cell associated with a particular disease state.

In one embodiment, the antigen binding domain binds to a tumor antigen, such as an antigen that is specific for a tumor or cancer of interest. In one embodiment, the tumor antigen of the present invention comprises one or more antigenic cancer epitopes.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof.

In some instances, it is beneficial for the antigen binding domain to be derived from the same species in which the CAR will ultimately be used in. For example, for use in humans, it may be beneficial for the antigen binding domain of the CAR to comprise a human antibody, humanized antibody as described elsewhere herein, or a fragment thereof.

It is also beneficial that the antigen binding domain is operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

Transmembrane Domain

With respect to the transmembrane domain, the CAR can be designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Intracellular Domain

The intracellular domain or otherwise the cytoplasmic domain of the CAR includes a similar or the same intracellular domain as the chimeric intracellular signaling molecule described elsewhere herein, and is responsible for activation of the cell in which the CAR is expressed.

In one embodiment, the intracellular domain of the CAR includes a domain responsible for signal activation and/or transduction.

Examples of an intracellular domain for use in the invention include, but are not limited to, the cytoplasmic portion of the T cell receptor (TCR) and any co-stimulatory molecule that acts in concert to initiate signal transduction following antigen receptor engagement, as well as any derivative or variant of these elements and any synthetic sequence that has the same functional capability.

Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

In one embodiment, the intracellular domain of the CAR includes any portion of a co-stimulatory molecule, such as at least one signaling domain from CD3, CD27, CD28, ICOS, 4-1BB, PD-1, T cell receptor (TCR), any derivative or variant thereof, any synthetic sequence thereof that has the same functional capability, and any combination thereof.

Between the antigen binding domain and the transmembrane domain of the CAR, or between the intracellular domain and the transmembrane domain of the CAR, a spacer domain may be incorporated. As used herein, the term "spacer domain" generally means any oligo- or polypeptide that functions to link any domain, such as linking the transmembrane domain to, either the antigen binding domain or, the intracellular domain in the polypeptide chain. The spacer domain may be on one or both ends of the CAR. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

Human Antibodies

It may be preferable to use human antibodies or fragments thereof when using bispecific antibodies or the antigen binding domains of a CAR. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The bispecific antibody can also include an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated by reference herein in their entirety.

Vectors

A vector may be used to introduce the chimeric intracellular signaling molecule or the CAR into a T cell as described elsewhere herein. In one aspect, the invention includes a vector comprising a nucleic acid sequence encoding a chimeric intracellular signaling molecule and, optionally, a nucleic acid sequence encoding a bispecific antibody as described herein. In another aspect, the invention includes a vector comprising a nucleic acid sequence encoding a CAR and, optionally, a nucleic acid sequence encoding a bispecific antibody as described herein. In one embodiment, the vector comprises a plasmid vector, viral vector, retrotransposon (e.g. piggyback, sleeping beauty), site directed insertion vector (e.g. CRISPR, zn finger nucleases, TALEN), or suicide expression vector, or other known vector in the art.

All constructs mentioned above are capable of use with 3rd generation lentiviral vector plasmids, other viral vectors, or RNA approved for use in human cells. In one embodiment, the vector is a viral vector, such as a lentiviral vector. In another embodiment, the vector is a RNA vector.

The production of any of the molecules described herein can be verified by sequencing. Expression of the full length proteins may be verified using immunoblot, immunohistochemistry, flow cytometry or other technology well known and available in the art.

The present invention also provides a vector in which DNA of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

The expression of natural or synthetic nucleic acids is typically achieved by operably linking a nucleic acid or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, N.Y.), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1a promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Introduction of Nucleic Acids

Methods of introducing and expressing genes, such as the chimeric intracellular signaling molecule or the CAR, into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, N.Y.). Nucleic acids can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). Nucleic acids can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. RNA vectors include vectors having a RNA promoter and/or other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the molecules described herein, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, one or more of the nucleic acid sequences described elsewhere herein are introduced by a method selected from the group consisting of transducing the population of cells, transfecting the population of cells, and electroporating the population of cells. In one embodiment, a population of cells comprises one or more of the nucleic acid sequences described herein.

In one embodiment, the nucleic acids introduced into the cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric intracellular signaling molecule and/or a bispecific antibody.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

Some in vitro-transcribed RNA (IVT-RNA) vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In one aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Generating Metabolically Enhanced T Cells

The invention includes a method of metabolically enhancing a tumor specific T cell, comprising introducing a CAR into a T cell, wherein the CAR comprises an antigen binding domain, a transmembrane domain and an intracellular domain of a co-stimulatory molecule, arming the CAR T cell with a bispecific antibody, wherein the bispecific antibody binds to a target on a tumor cell and the CAR T cell, and stimulating at least one co-stimulatory molecule on the armed CAR T cell, wherein the stimulation activates the intracellular domain of the co-stimulatory molecule thereby metabolically enhancing the armed T cell. In one embodiment, introducing the CAR into the T cell comprises introducing a nucleic acid sequence encoding the CAR, such as by electroporating a mRNA encoding the CAR. In another embodiment, arming the CAR T cell comprises contacting the CAR T cell with the bispecific antibody. In yet another embodiment, arming the CAR T cell comprises introducing a nucleic acid sequence encoding the bispecific antibody, such as by electroporating a mRNA encoding the bispecific antibody. In still another embodiment, stimulating the armed CAR T cell improves cytotoxicity and resistance to immunosuppression of the armed CAR T cell when in a tumor microenvironment. In yet another embodiment, the method further comprises irradiating the CAR T cell with up to 2500 rad to inhibit proliferation of the CAR T cell without inhibiting cytokine secretion or inducing cytotoxicity.

In yet another embodiment, arming the CAR T cell comprises arming the CAR T cell with two or more bispecific antibodies, wherein the CAR T cell displays the two or more bispecific antibodies. In still another embodiment, the two or more bispecific antibodies specifically bind the CAR T cell. In another embodiment, the bispecific antibodies comprise a combination of antibodies selected from the group consisting of anti-CD3, anti-IgD Fc, and anti-IgA Fc. In certain embodiments, the bispecific antibody is chemically heteroconjugated to a polyclonal antibody specific for a tumor-associated antigen (TAA), wherein the T cells specifically bind the TAA polyclonal antibody.

Sources of T Cells

The metabolically enhanced T cells may be generated from any source of T cells. In one embodiment, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, a population of cells comprise the T cells of the present invention. Examples of a population of cells include, but are not limited to, peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

T cells generated by any method described herein may be expanded ex vivo. In one embodiment, T cells or a population of cells comprising T cells are cultured for expansion. Generally, T cells are expanded by contact with a surface having attached thereto an agent that stimulates a CD3/TCR complex associated signal and a ligand that stimulates a co-stimulatory molecule on the surface of the T cells with or without IL-2.

Methods for expanding T cells are described herein. For example, the T cells can be expanded by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial intergers therebetween. In one embodiment, the T cells expand in the range of about 20 fold to about 50 fold.

The T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing one or more of the molecules described elsewhere herein into the T cells.

The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

In one embodiment, the T cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The T cell culturing medium may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

Therapy

The metabolically enhanced T cells described herein are useful in a variety of treatment modalities for treatment of a number of disease states whether the T cell is metabolically enhanced by virtue of expression of either a chimeric intracellular signaling molecule or a CAR. Thus, irrespective of whether the T cell expresses a chimeric intracellular signaling molecule or a CAR, the T cell is referred to herein as a metabolically enhanced T cell. A composition comprising a metabolically enhanced T cell can be generated according to the methods described elsewhere herein. This metabolically enhanced T cell may be included in a composition for therapy as now described.

In one aspect, the composition comprises the metabolically enhanced T cell comprising the chimeric intracellular signaling molecule or CAR described herein. In another aspect, the composition comprises the metabolically enhanced cell further comprising the bispecific antibody described herein. The composition may include a pharmaceutical composition and further include a pharmaceutically acceptable carrier. A therapeutically effective amount of the pharmaceutical composition comprising the modified cells may be administered.

In one aspect, the invention includes a method of treating a disease or condition associated with enhanced immunity in a subject comprising administering to the subject a therapeutically effective amount of a pharmaceutical composition comprising the metabolically enhanced T cell described herein. In another aspect, the invention includes a method of treating a condition in a subject, comprising administering to the subject a therapeutically effective amount of a pharmaceutical composition comprising the metabolically enhanced T cell described herein. In another aspect, the invention includes a method for stimulating a T cell-mediated immune response to a target cell or tissue in a subject comprising administering to a subject a therapeutically effective amount of a pharmaceutical composition comprising the metabolically enhanced T cell described herein. In yet another aspect, the invention includes use of the metabolically enhanced T cell described herein in the manufacture of a medicament for the treatment of an immune response in a subject in need thereof. In these embodiments, the T cell comprises a chimeric intracellular signaling molecule, wherein the chimeric intracellular signaling molecule comprises an intracellular domain of a co-stimulatory molecule and substantially lacks an extracellular ligand-binding domain. In another embodiment, the T cell further comprises a bispecific antibody. In yet another embodiment, the T cell further comprises a CAR.

In one aspect, the invention includes a method of treating a disease or condition associated with a tumor or cancer in a subject comprising administering to the subject a therapeutically effective amount of a pharmaceutical composition comprising the metabolically enhanced T cell described herein. In another aspect, the invention includes a method of treating a solid tumor in a subject, comprising administering to the subject a therapeutically effective amount of a pharmaceutical composition comprising the metabolically enhanced T cell described herein. In another aspect, the invention includes a method for stimulating a T cell-mediated immune response to a target tumor cell or tumor tissue in a subject comprising administering to a subject a therapeutically effective amount of a pharmaceutical composition comprising the metabolically enhanced T cell described herein. In yet another aspect, the invention includes use of the metabolically enhanced T cell described herein in the manufacture of a medicament for the treatment of a tumor or cancer in a subject in need thereof. In these embodiments, the T cell comprises a CAR and a bispecific antibody, wherein the CAR comprises an antigen binding domain, a transmembrane domain and an intracellular domain of a co-stimulatory molecule, and the bispecific antibody binds to a target on a tumor cell and the T cell. Another embodiment includes a method for stimulating a T cell-mediated immune response to a target tumor cell or tumor tissue in a subject comprising administering to a subject a therapeutically effective amount of a pharmaceutical composition comprising the T cell of the present invention.

The metabolically enhanced T cells as described herein can be administered to an animal, preferably a mammal, even more preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the metabolically enhanced T cells of the present invention can be used for the treatment of any condition in which a diminished or otherwise inhibited immune response, especially a cell-mediated immune response, is desirable to treat or alleviate the disease. In one aspect, the invention includes treating a condition, such as an autoimmune disease, in a subject, comprising administering to the subject a therapeutically effective amount of a pharmaceutical composition comprising a population of the cells described herein.

Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The metabolically enhanced T cells described herein may also be used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The metabolically enhanced T cells of the present invention can be used to treat cancers. Cancers include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyngioma, ependymoma, pinealoma, hemangioblastoma, acoustic neuroma, oligodendroglioma, menangioma, neuroblastoma, retinoblastoma and brain metastases).

The metabolically enhanced T cells of the invention can be administered in dosages and routes and at times to be determined in appropriate pre-clinical and clinical experimentation and trials. Cell compositions may be administered multiple times at dosages within these ranges. Administration of the metabolically enhanced T cells of the invention may be combined with other methods useful to treat the desired disease or condition as determined by those of skill in the art.

The metabolically enhanced Tcells of the invention may be autologous, allogeneic or xenogeneic with respect to the subject administered therein that is undergoing therapy.

The administration of the metabolically enhanced T cells of the invention may be carried out in any convenient manner known to those of skill in the art. The metabolically enhanced T cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the metabolically enhanced T cells of the invention are injected directly into a site of inflammation in the subject, a local disease site in the subject, alymph node, an organ, a tumor, and the like.

Pharmaceutical Compositions

Pharmaceutical compositions of the present invention may comprise the metabolically enhanced T cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-immune response effective amount", "an immune response-inhibiting effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer the metabolically enhanced T cells to a subject and then subsequently redraw blood (or have an apheresis performed), metabolically enhance T cells therefrom according to the present invention, and reinfuse the patient with these metabolically enhanced T cells. This process can be carried out multiple times every few weeks. In certain embodiments, metabolically enhanced T cells can be obtained from blood draws from about 10 ml to about 400 ml. In certain embodiments, metabolically enhanced T cells are obtained from blood draws of about 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, T cells are metabolically enhanced using the methods described herein, and stimulated, activated or expanded using the methods described herein or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or treatments for PML patients. In further embodiments, the metabolically enhanced T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the metabolically enhanced T cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook et al., (2012) Molecular Cloning, Cold Spring Harbor Laboratory); "Oligonucleotide Synthesis" (Gait, M. J. (1984). Oligonucleotide synthesis. IRL press); "Culture of Animal Cells" (Freshney, R. (2010). Culture of animal cells. Cell Proliferation, 15(2.3), 1); "Methods in Enzymology" "Weir's Handbook of Experimental Immunology" (Wiley-Blackwell; 5 edition (Jan. 15, 1996); "Gene Transfer Vectors for Mammalian Cells" (Miller and Carlos, (1987) Cold Spring Harbor Laboratory, New York); "Short Protocols in Molecular Biology" (Ausubel, et al., Current Protocols; 5 edition, Nov. 5, 2002); "Polymerase Chain Reaction: Principles, Applications and Troubleshooting", (Babar, M., VDM Verlag Dr. Müller, Aug. 17, 2011); "Current Protocols in Immunology" (Coligan, John Wiley & Sons, Inc., Nov. 1, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Production of Bispecific Antibodies.

Bispecific antibodies (BiAbs) were produced by chemical heteroconjugation of OKT3 and Rituxan (a humanized anti-CD20 IgG1, Genentech Inc., South San Francisco, CA), OKT3 and Erbitux (a humanized anti-epidermal growth factor receptor (EGFR) IgG1, ImClone LLC., Branchburg, NJ) or OKT3 and Herceptin (a humanized anti-HER2 IgG1, Genentech Inc., South San Francisco, CA) as described (Gall J M, et al., *Experimental Hematology* 2005, 33:452-459; Reusch U, et al., *Journal of Hematotherapy and Stem Cell Research* 2001, 10:247-260).

Arming of T Cells.

Activated T cells were armed with anti-OKT3×anti-CD20 BiAb (CD20Bi) or anti-OKT3×anti-EGFR BiAb (EGFRBi) using a previously optimized concentration (50 ng/$10^6$ ATC) (Sen M, et al., *Journal of Hematotherapy and Stem Cell Research* 2001, 10:247-260).

Cytotoxicity/$^{51}$Cr Release Assay.

To target adherent cells, cells were plated in 96-well flat-bottom microtiter plates at $4×10^4$ cells/well and allowed to adhere overnight. The cells were labeled with $^{51}$Cr at 20 μCi/mL in the labeling media (50% FBS in complete RPMI-1640) for 5 hours at 37° C., and washed with complete RPMI-1640 to remove unincorporated isotope. For non-adherent cell targeting, Daudi cells were labeled with $^{51}$Cr at 100 μCi/$10^6$ cells in a 15 mL conical tube for 2 hours at 37° C., washed with complete RPMI-1640, and plated in 96-well round-bottom microtiter plates at $1×10^4$ cells/well. Effectors (unarmed CART19 or ATC and armed CART19 or ATC) were then added to achieve effector:target (E:T) ratios of 10:1. Co-cultures were incubated for 4 hours (Daudi) or 18 hours (Adherent cell lines) and the supernatant was collected for liquid scintillation counting to quantitate the amount of released $^{51}$Cr. Percent cytotoxicity was calculated as follows: (experimental cpm−spontaneous cpm)/(maximum cpm−spontaneous cpm)×100. Means and standard errors were calculated from four to six replicates per sample.

The results of the experiments are now described.

Figure 2:
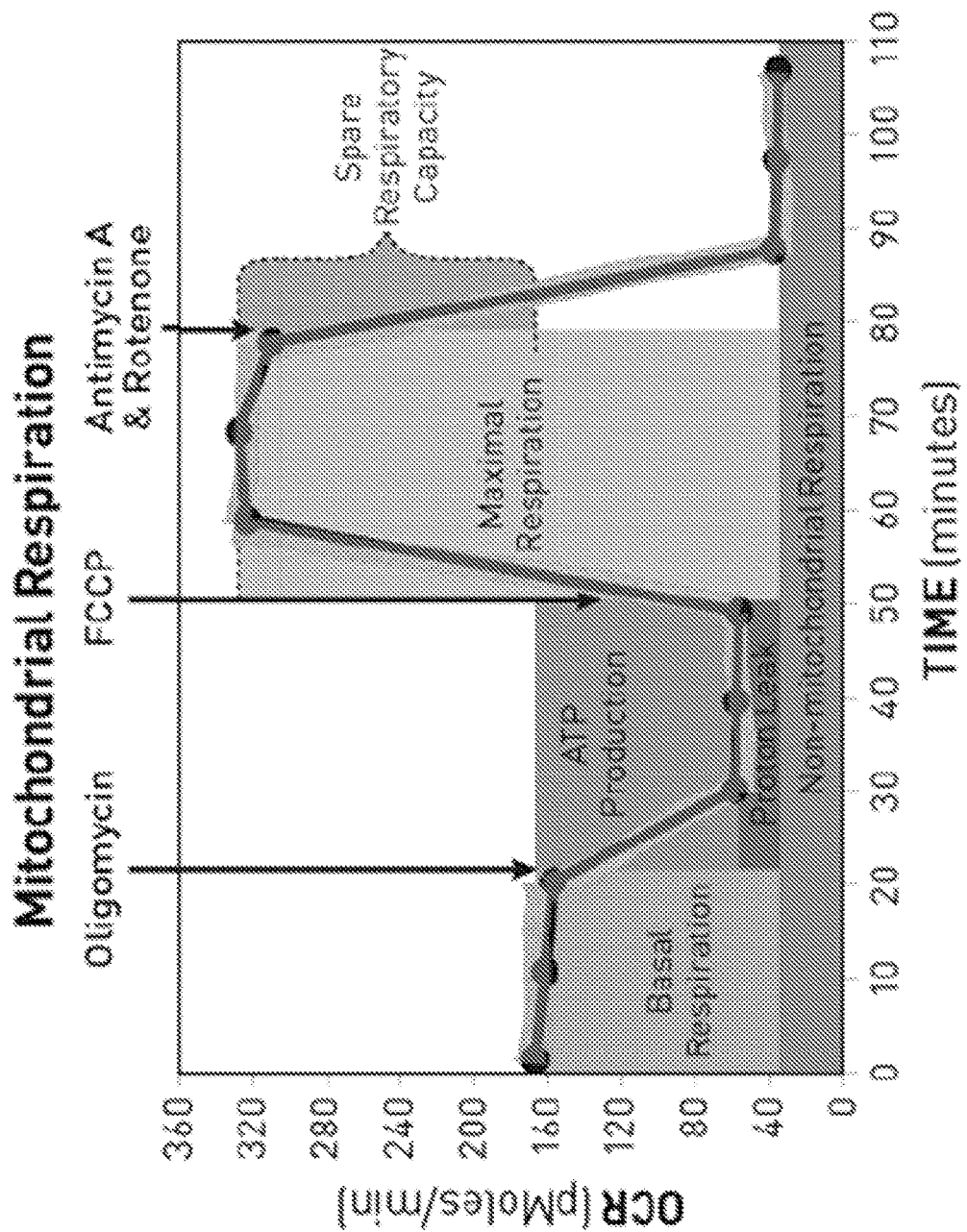
FIG. 2 is a diagram showing a sea horse assay used to measure metabolic features of modified T cells. OCR-Mitochondrial respiration by oxidative phosphorylation; ECAR-Glycolytic production of ATP; Spare Respiratory Capacity is associated with enhanced survival and persistence under stress.

T cells modified with CARs were capable of intracellular signaling and surprising survival effects when exposed to hypoxic conditions. FIG. 1 is a panel of graphs showing survival of CART cells in hypoxic conditions. Survival was differentially affected depending on the type of CAR structure expressed in the T cells. The differentials in survival depended on the co-stimulatory endodomain. The effect of different co-stimulatory endodomains on metabolic activity in T cells expressing CARs was tested in a sea-horse assay as shown in FIG. 2.

Figure 3:
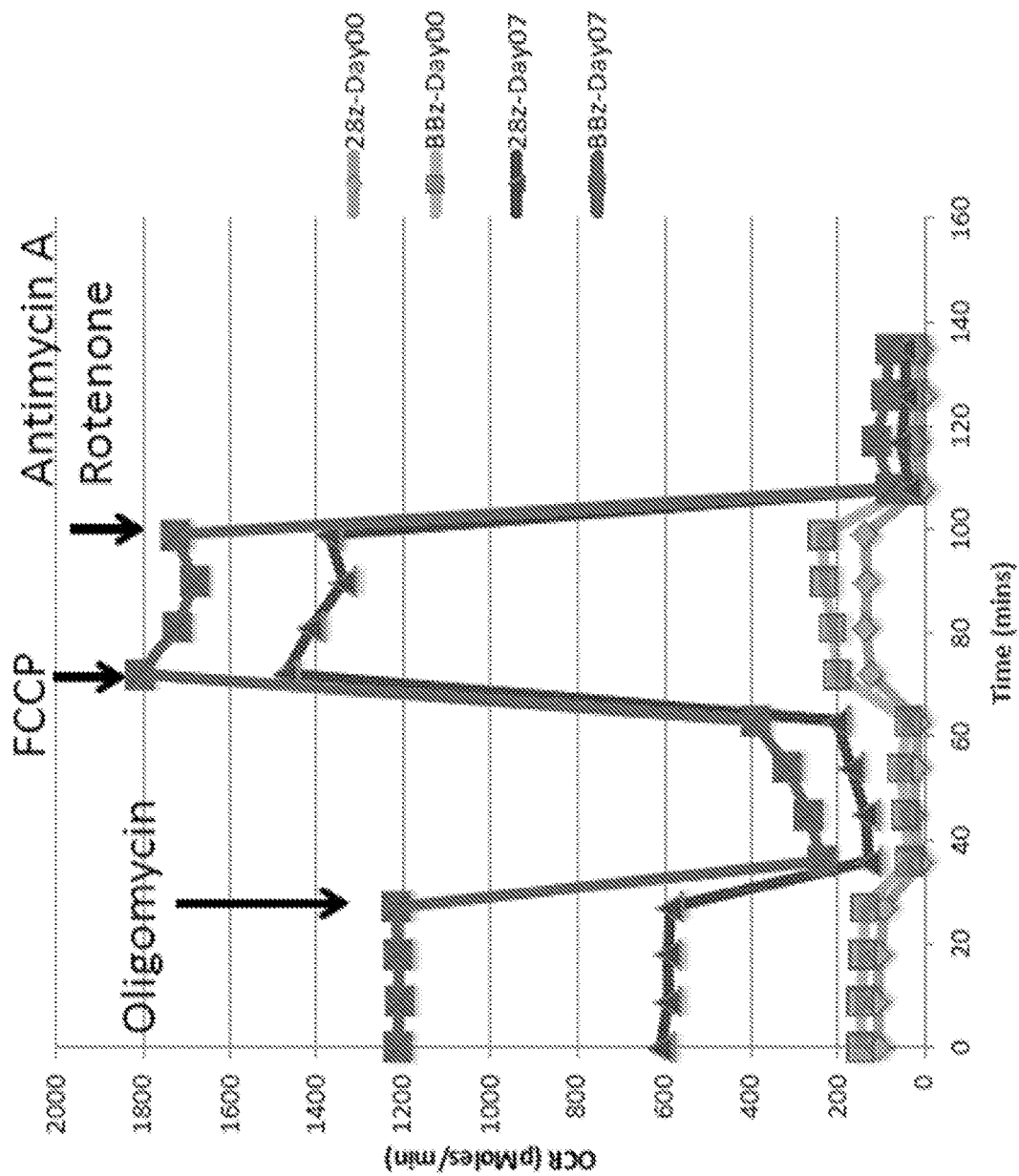
FIG. 3 is a graph showing metabolic reprogramming of modified T cells expressing CARs with either CD28 or 4-1BB signaling domains.

Metabolic activity of T cells expressing either a CD28z or 4-1BBz co-stimulatory endodomain of a CAR is shown in FIG. 3. 4-1BBz CART cells had ligand independent signaling and were reprogrammed to T central memory (Tcm) cells, while CD28z CAR T cells were reprogrammed to effector memory (Tem) cell. 4-1BBz CAR T cells had lower levels of surface molecules, such as PD1, TIM3 and LAG3, which is usually associated with exhaustion. They also had higher metabolic activity after surrogate antigen activation and survived longer under conditions of stringent hypoxia (FIG. 3).

Figure 4:
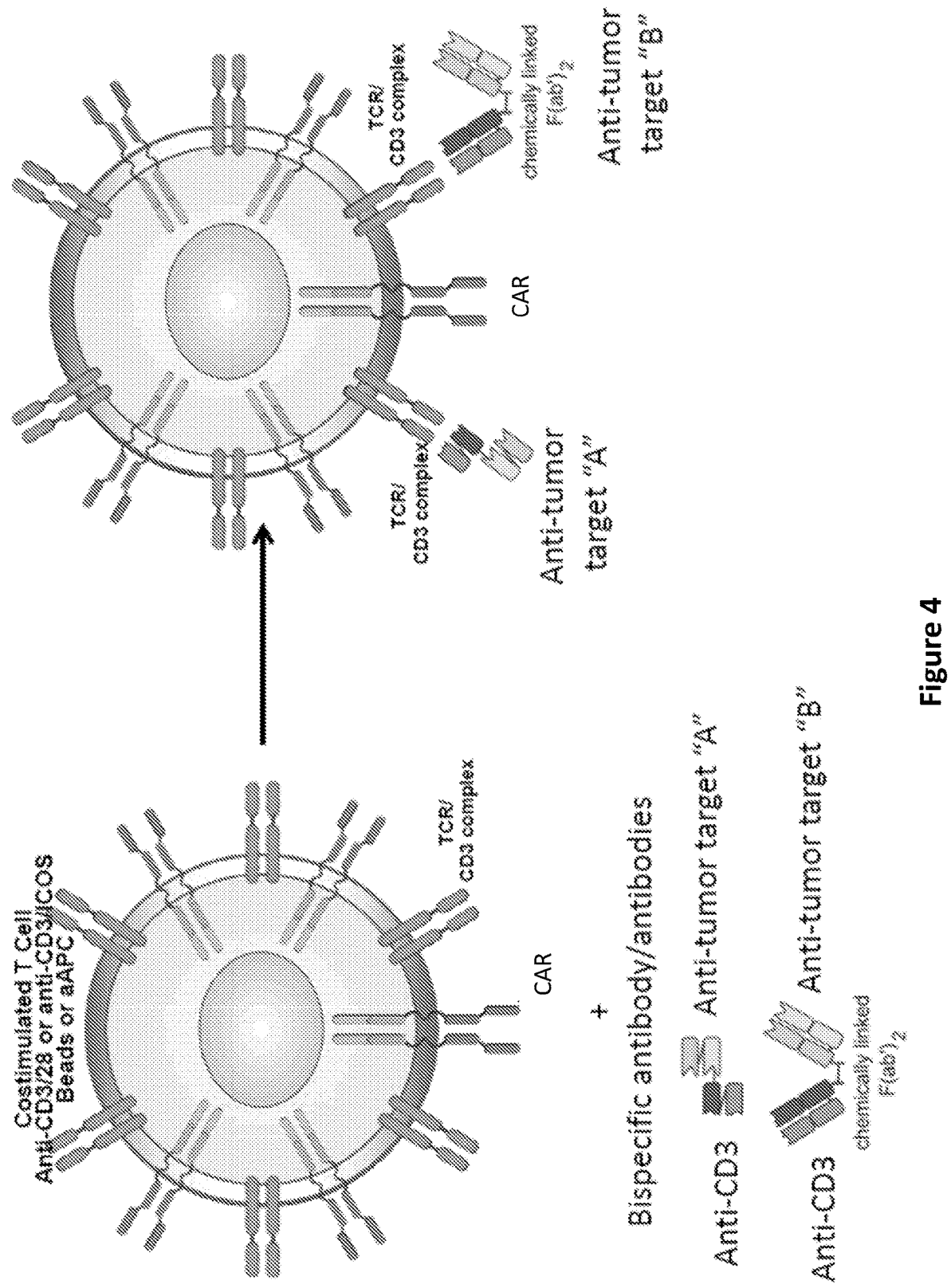
FIG. 4 is an illustration of a bispecific antibody (Fab CD3 with Fab anti-Target A or B) armed T cell with a CAR introduced by a lentiviral vector. Data utilized whole IgG molecules with a Fc-Fc permanent covalent link.
Figure 5:
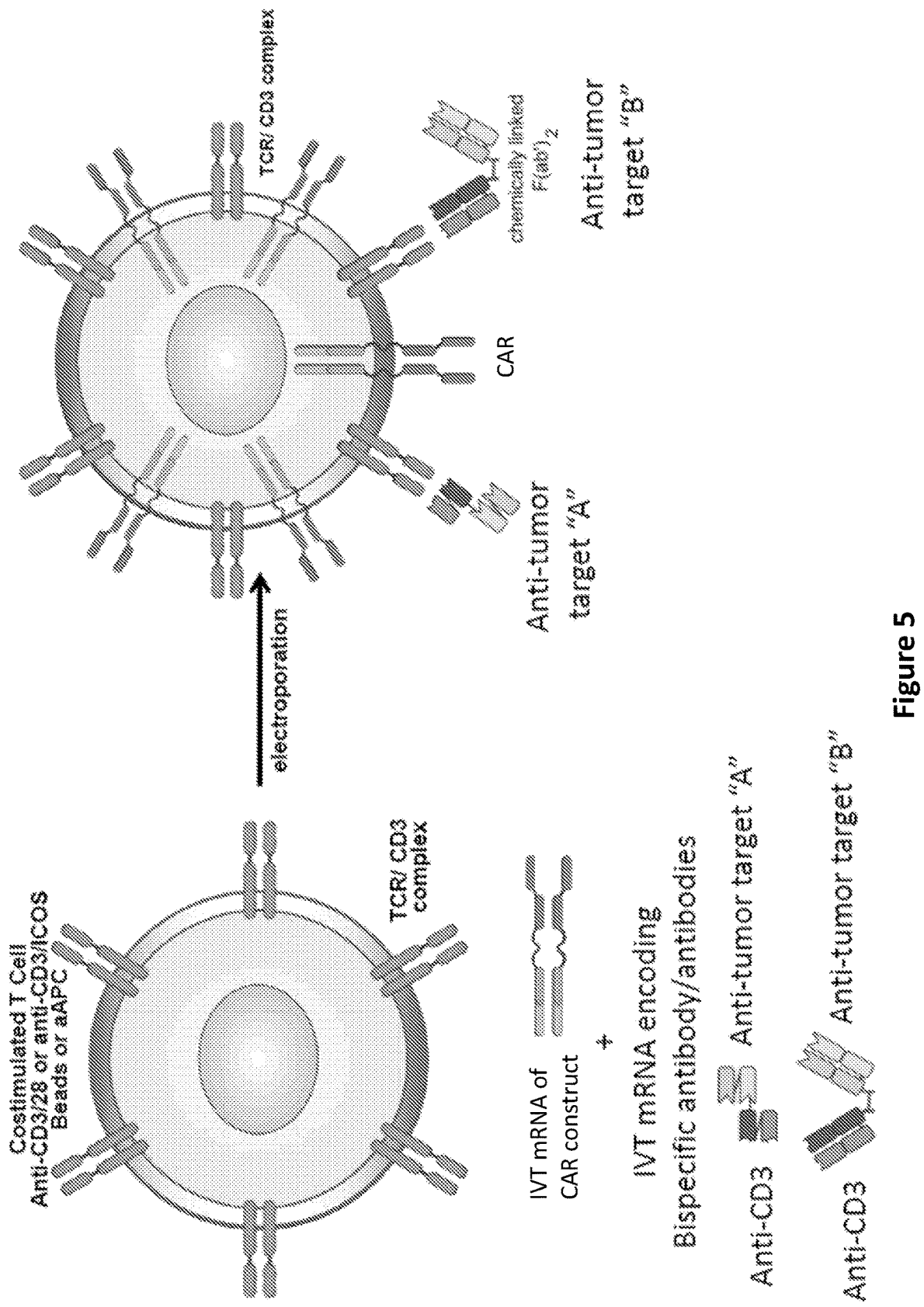
FIG. 5 is an illustration of a bispecific antibody armed T cell with a CAR introduced by mRNA electroporation.

Use of CARs was shown to metabolically enhance and possibly decrease alloreactivity of modified T cells. Such findings support the use of "universal T cells" or even 3rd party T cells. CARs may be introduced into T cells via multiple methods, such as with a lentiviral vector (FIG. 4) or mRNA electroporation (FIG. 5). Potential targets of the CAR include any tumor associated antigen, such as EGFR, HER2/NEU, PSMA, BCMA, GD2, mesothelin, etc. The intracellular portion of the CAR used in the assays described herein may include one or more signaling domains that are chosen to enhance T cell metabolism for any given tumor microenvironment, e.g. 4-1BB, CD27, Ox40, ICOS or CD28. Displaying bispecific scFv or covalent coupling of bispecific antibodies onto CART cells through exposure to the antibodies or "arming" just prior to infusion into the patient may also be useful for enhancing cytolytic activity of the T cells.

As an alternative to the use of a lentiviral vector, short lived T cells may be metabolically enhanced by introducing an mRNA encoding a CAR by electroporation (FIG. 5). Briefly, T cells are cultured and costimulated with anti-CD3 and anti-CD28 antibodies with or without IL-2. The T cells are then electroporated with in vitro transcribed mRNA to introduce the CAR. The CART cells are then armed with bispecific antibodies. Alternatively, in vitro transcribed mRNA encoding bispecific scFv or bispecific antibodies may be electroporated into the CART cells just prior to infusion. The bispecific antibody armed CART cells can then be injected intravenously or intratumorally into the patient.

Figure 6:
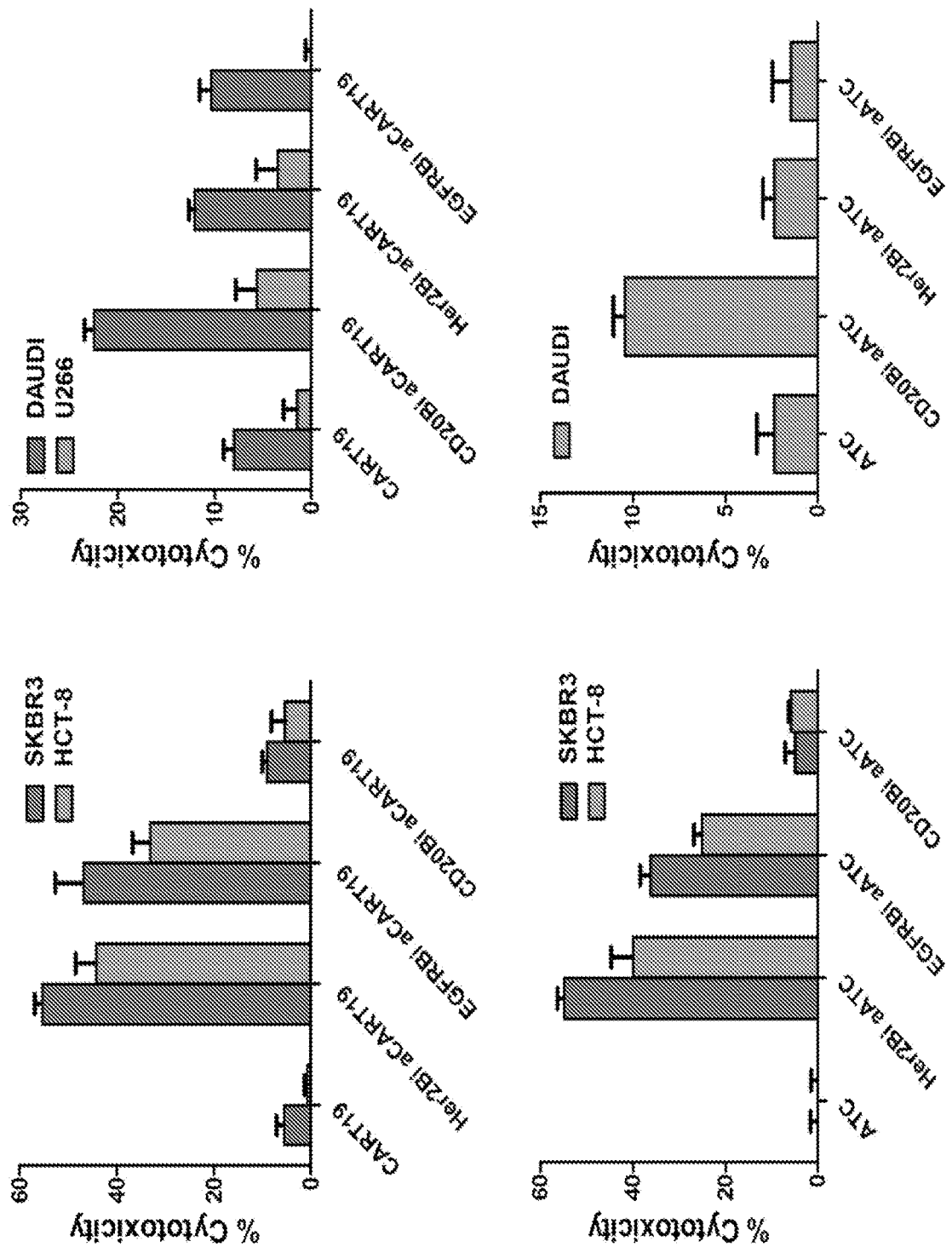
FIG. 6 is a panel of graphs showing specific cytotoxicity of unarmed or anti-HER2 bispecific antibody (HER2Bi) and anti-EGFR bispecific antibody (EGFRBi) armed CART19 cells or non-CART19 cells (ATC) in a $^{51}Cr$ release assay against HER2 and EGFR expressing cell lines. Assays were performed in triplicate using armed or unarmed CART19 cells against HER2 expressing SK-BR-3, EGFR expressing HCT-8 or CD19$^+$/CD20$^+$ (Daudi) and CD19$^-$/CD20$^-$ (U266) cell lines at effector/target ratio of 10:1 for 18 hours to measure cytotoxicity.

Specific cytotoxicities of armed (with bispecific antibodies) or unarmed (without bispecific antibodies) CART cells and non-CART cells are shown in FIG. 6. Effector cells included unarmed CART19 cells and CART19 cells armed with anti-HER2, anti-EGFR or anti-CD20 bispecific antibodies (upper graphs), and unarmed non-CART cells and non-CART cells armed with anti-HER2, anti-EGFR or anti-CD20 bispecific antibodies (lower graphs). Both CART19 cells and non-CART cells demonstrated specific cytotoxicities against the target cells.

Figure 7:
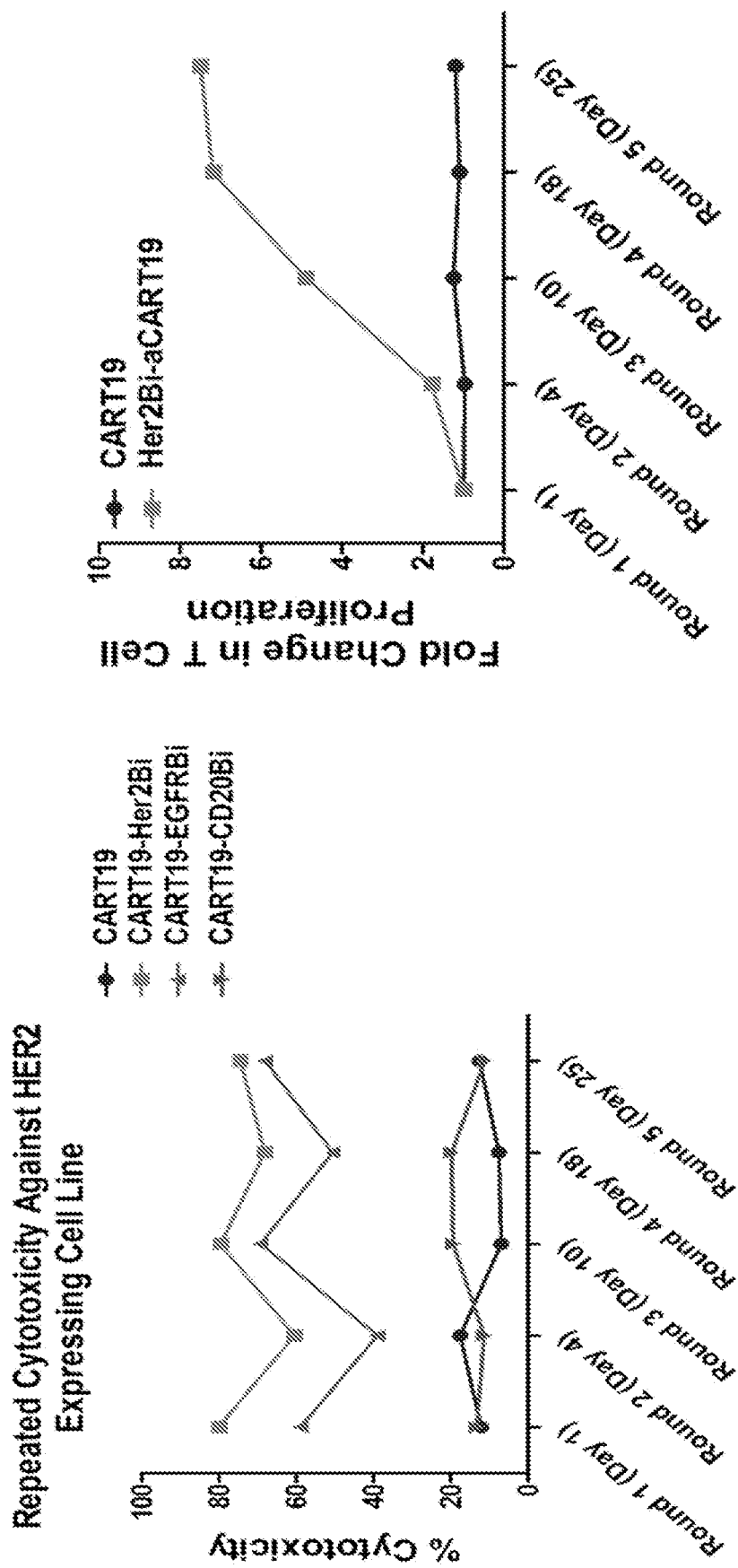
FIG. 7 is a panel of graphs showing specific cytotoxicity by armed and unarmed CART19 cells measured over the course of repeated exposures to SK-BR-3 tumor targets (HER2 and EGFR positive breast cancer cell line) at days 1, 4, 10, 18 and 25 at an effector/target ratio of 10:1 in a $^{51}Cr$ release assay. Right graph shows fold change in proliferation of CART19 cells during a repeated killing assay. The mean fold change in proliferation of armed versus unarmed cells after exposure to SK-BR-3 targets at days 1, 4, 10, 18, and 25. Cell counts and viability were assessed at the indicated days using trypan blue during 4 weeks of culture. Repeated cytotoxicity (left panel) occurred when the appropriate tumor-associated antigen (TAA) was present and proliferation occurred when there was engagement of the appropriate (HER2Bi) was on the CART cell.
Figure 8B:
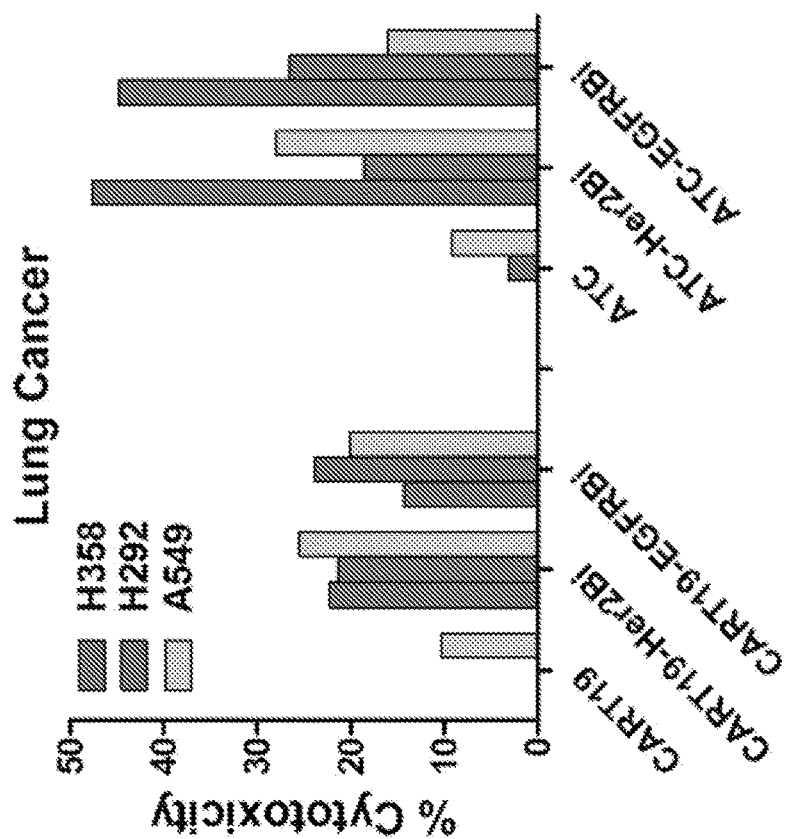
FIG. 8B is a graph showing specific cytotoxicity of unarmed or HER2Bi and EGFRBi armed CART19 cells and non-CART19 cells (ATC) against lung cancer cells expressing HER2 and EGFR. Armed or unarmed CART19 cells plated onto HER2 and EGFR expressing lung cell lines in triplicates at an effector/target ratio of 10:1 for 18 hours for cytotoxicity by $^{51}Cr$ release assay.
Figure 8A:
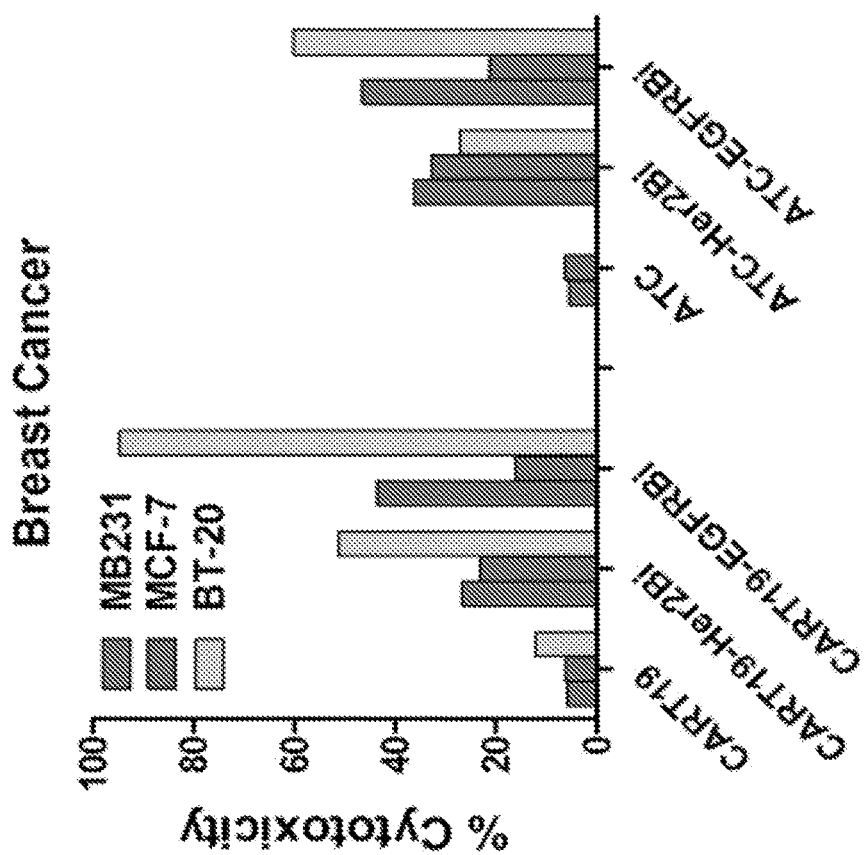
FIG. 8A is a graph showing specific cytotoxicity of unarmed or HER2Bi and EGFRBi armed CART19 cells and non-CART19 cells (ATC) against breast cancer cells expressing HER2 and EGFR. Average of triplicates are shown of armed or unarmed cells plated onto HER2 and EGFR expressing breast cancer cell lines at effector/target ratio of 10:1 for 18 hours for cytotoxicity by $^{51}Cr$ release assay.
Figure 8D:
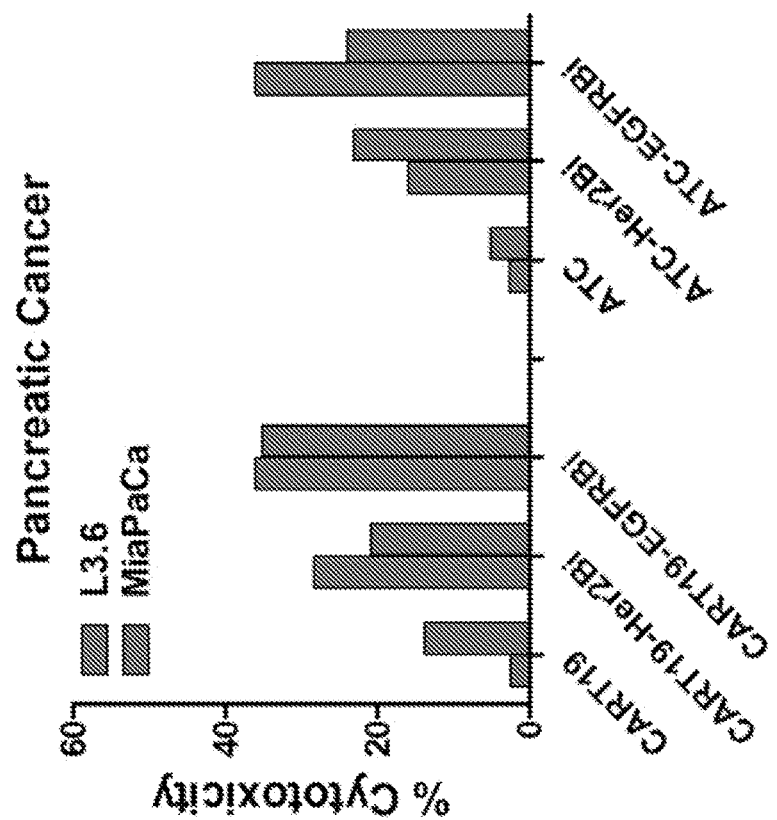
FIG. 8D is a graph showing specific cytotoxicity of unarmed or HER2Bi and EGFRBi armed CART19 cells and non-CART19 cells (ATC) against pancreatic cancer cells expressing HER2 and EGFR. Armed or unarmed CART19 cells plated onto HER2 and EGFR expressing cell lines in triplicates at an effector/target ratio of 10:1 for 18 hours for cytotoxicity by $^{51}Cr$ release assay.
Figure 8C:
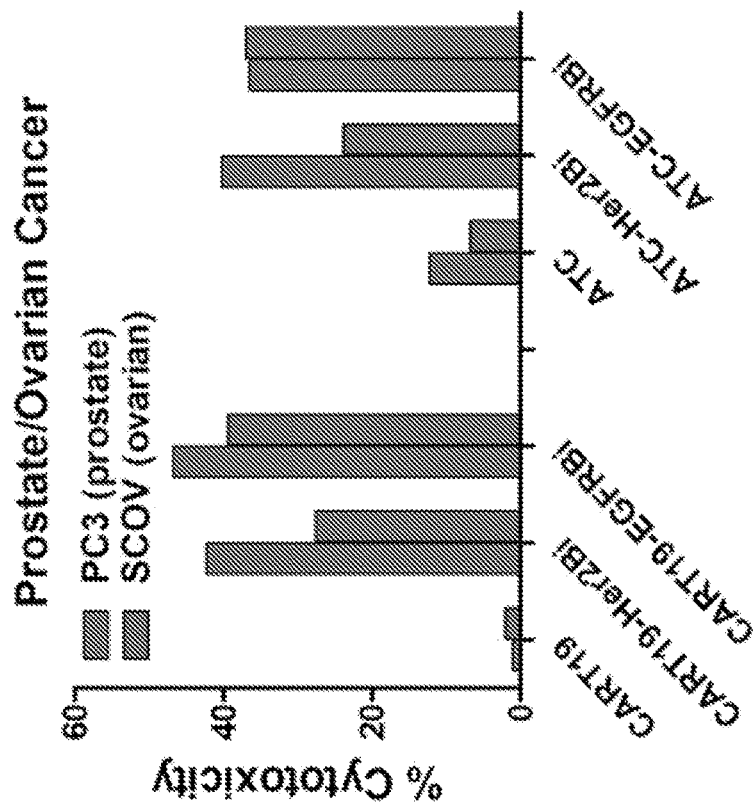
FIG. 8C is a graph showing specific cytotoxicity of unarmed or HER2Bi and EGFRBi armed CART19 cells and non-CART19 cells (ATC) against prostate/ovarian cancer cells expressing HER2 and EGFR. Armed or unarmed CART19 cells plated onto HER2 and EGFR expressing cell lines in triplicates at an effector/target ratio of 10:1 for 18 hours for cytotoxicity by $^{51}Cr$ release assay.
Figure 8E:
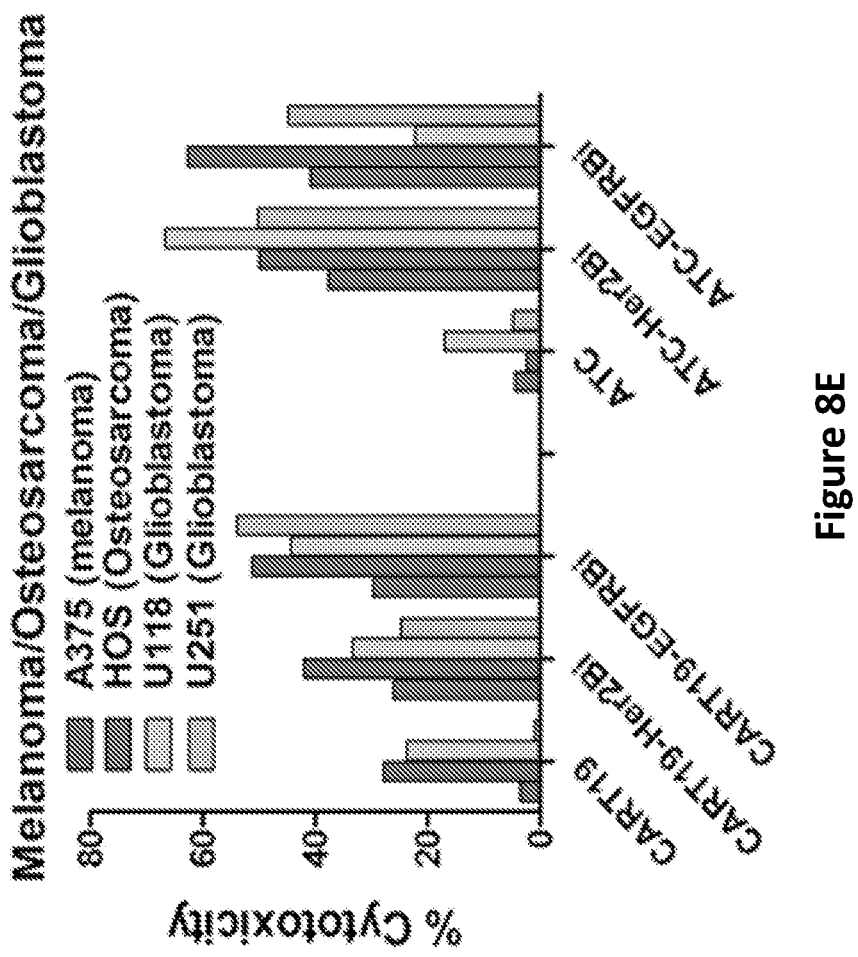
FIG. 8E is a graph showing specific cytotoxicity of unarmed or HER2Bi and EGFRBi armed CART19 cells and non-CART19 cells (ATC) against melanoma/osteosarcoma/glioblastoma cancer cells expressing HER2 and EGFR. Armed or unarmed CART19 cells plated onto HER2 and EGFR expressing cell lines in triplicates at an effector/target ratio of 10:1 for 18 hours for cytotoxicity by $^{51}Cr$ release assay.

Specific cytotoxicities (left graph of FIG. 7) of the unarmed and armed CART19 cells measured over the course of repeated exposures to SKBR3 at days 1, 4, 10, 18, and 25 demonstrated a high level of cytotoxicity toward target cells even after multiple rounds in the killing assay (without IL-2). The right panel of FIG. 7 shows enhanced proliferation demonstrated by CART19 cells during a repeated killing assay.

FIGS. 8A-8E show specific cytotoxicities of armed or unarmed CART19 cells and non-CAR T cells against various target cells expressing HER2 or EGFR. Effector cells were armed with anti-HER2 or anti-EGFR bispecific antibodies. CART19 cells armed with anti-HER2 bispecific antibodies were effective at killing even low expressing HER2 (MCF-7) or non-HER2 expressing breast cancer cell lines (Triple negative [HER2/ER/PR negative cell lines] MB231 and BT-20), i.e. ~20-50%.

Figure 9:
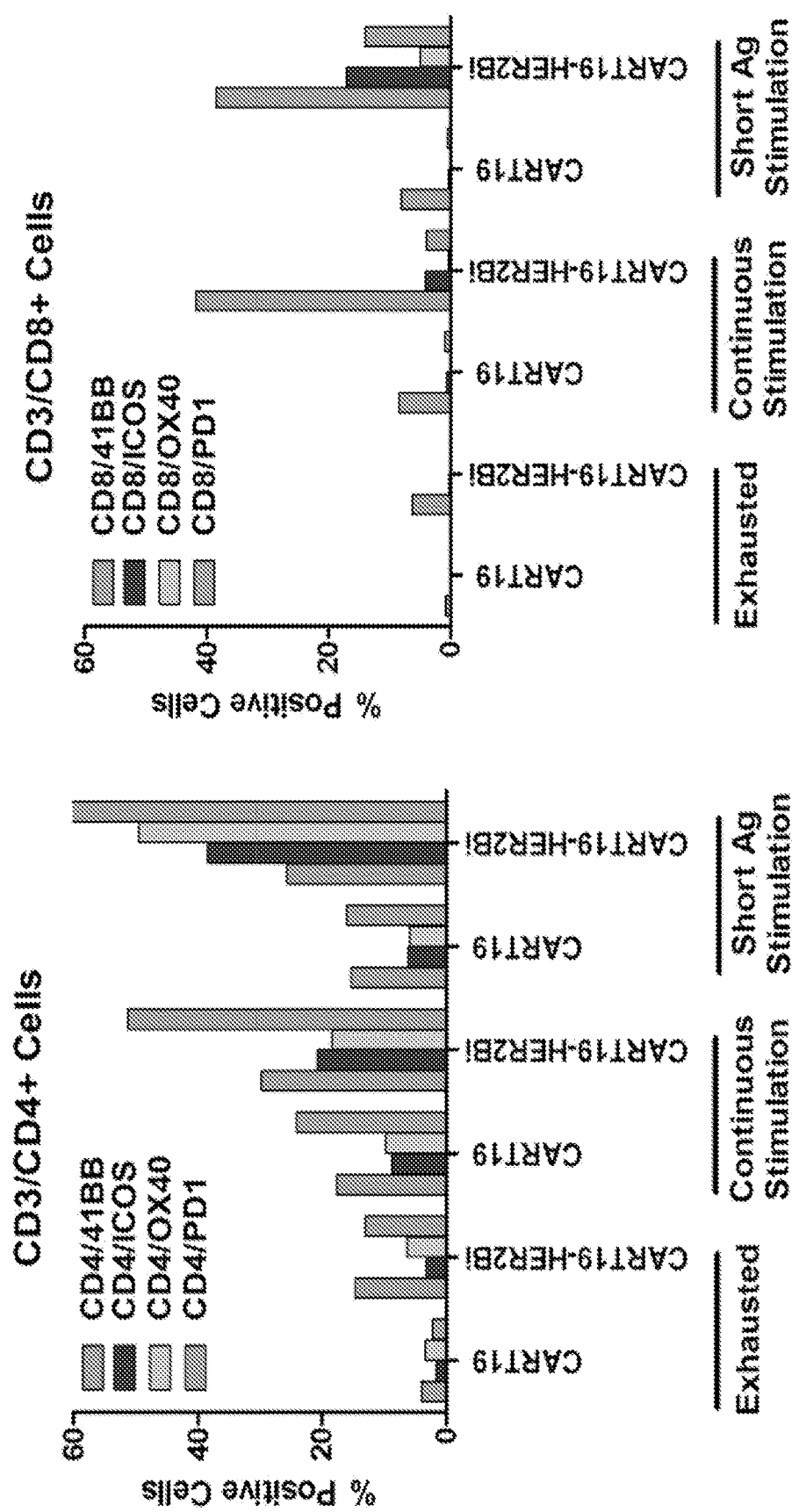
FIG. 9 is a panel of graphs showing activating and inhibitory co-receptor expression on CD4 and CD8 T cell populations with exhausted (lack of cytotoxicity), short term (24 h) or long term (120 h) antigen exposure to unarmed or armed CART19 cells.

FIG. 9 shows armed (HER2 bispecific antibodies) CART19 cells increased expression of activating and inhibitory co-receptors, e.g., 4-1BB, ICOS, OX40 and PD1, on CD4 and CD8 T cells.

Figure 10:
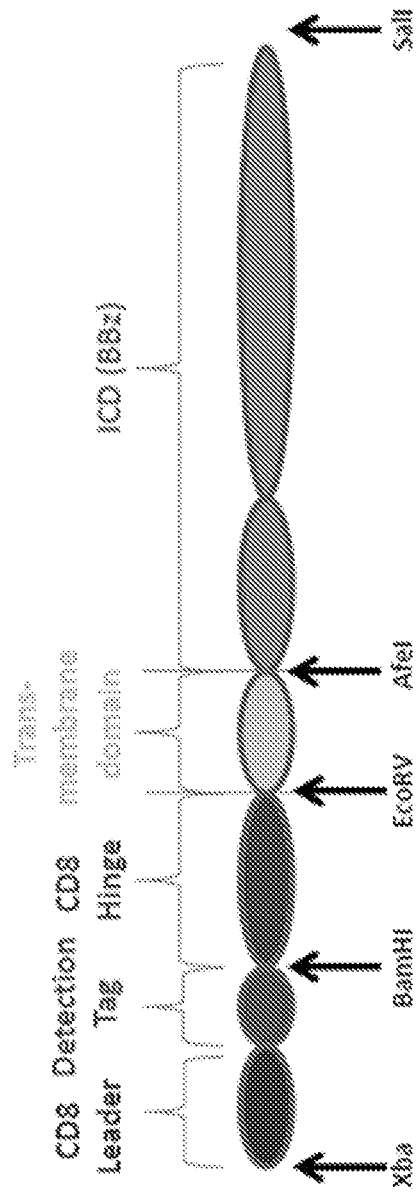
FIG. 10 is an illustration of a sequence and basic structure for a chimeric intracellular signaling molecule, eg., 4-1BBz. One example of a chimeric intracellular signaling molecule includes a fusion protein with a detectable tag, hinge/transmembrane domain, and intracellular domain.

Intracellular signaling domains from other co-stimulatory molecules may also have a positive effect on metabolic activity in T cells. The intracellular domain of the chimeric intracellular signaling molecule (FIG. 10) (SEQ ID NO:1) may be chosen from a co-stimulatory molecule that enhances T cell metabolism for any given tumor microenvironment, e.g. 4-1BB, CD27, Ox40, ICOS or CD28.

Figure 11:
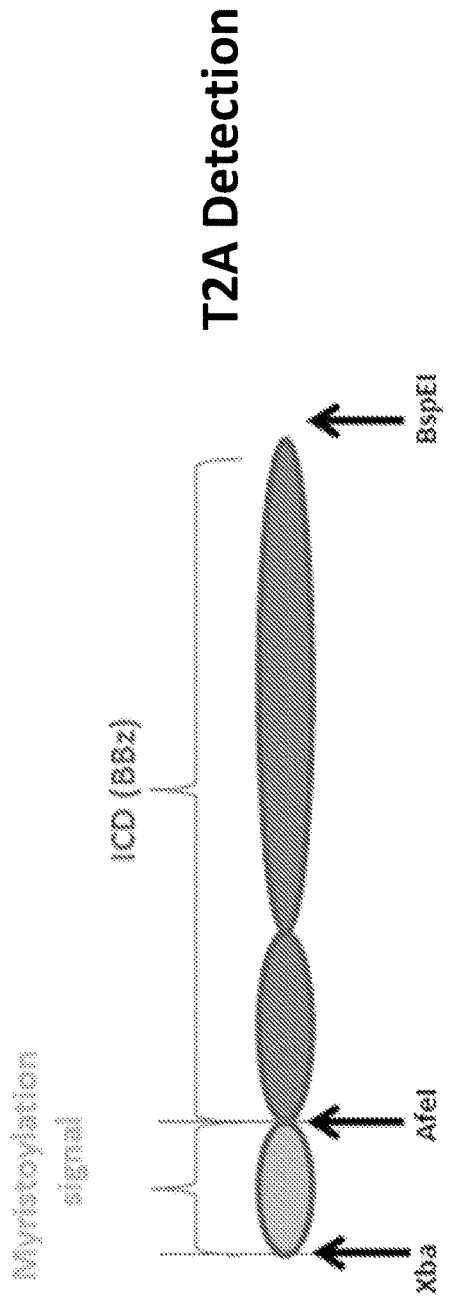
FIG. 11 is an illustration of a chimeric intracellular signaling molecule with a myristoylation signal. A chimeric intracellular signaling molecule that is not detectable on the surface of the cell would use a surrogate marker for detection, such as a fluorescent protein or cell surface molecule with linked expression through T2A or IRES elements.
Figure 12:
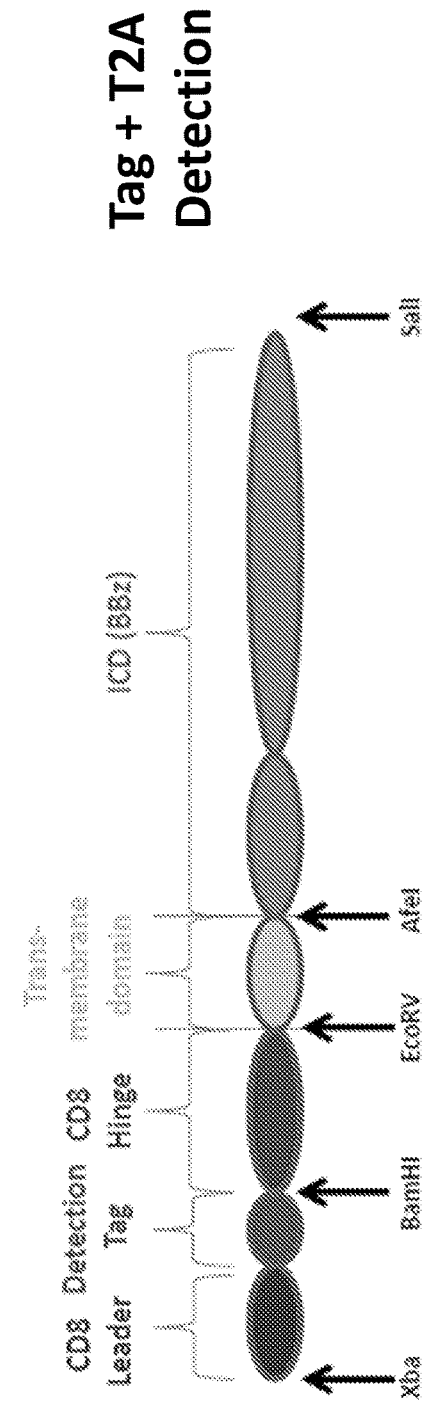
FIG. 12 is an illustration of a chimeric intracellular signaling molecule with a fusion tag for detection. Alternatively, a detectable surrogate marker is coexpressed using T2A or IRES systems and both are detectable markers for the chimeric intracellular signaling molecule.

It is envisioned that the chimeric intracellular signaling molecule includes a detectable tag for surface detection (FIG. 10), otherwise it cannot be detected on the surface of the T cells. Alternatively, a surrogate marker can be used instead of the detectable tag, such as a fluorescent protein or cell surface molecule coexpressed by a T2A or IRES system (FIG. 11). A detectable tag may also be used with a surrogate marker (FIG. 12)

Figure 13:
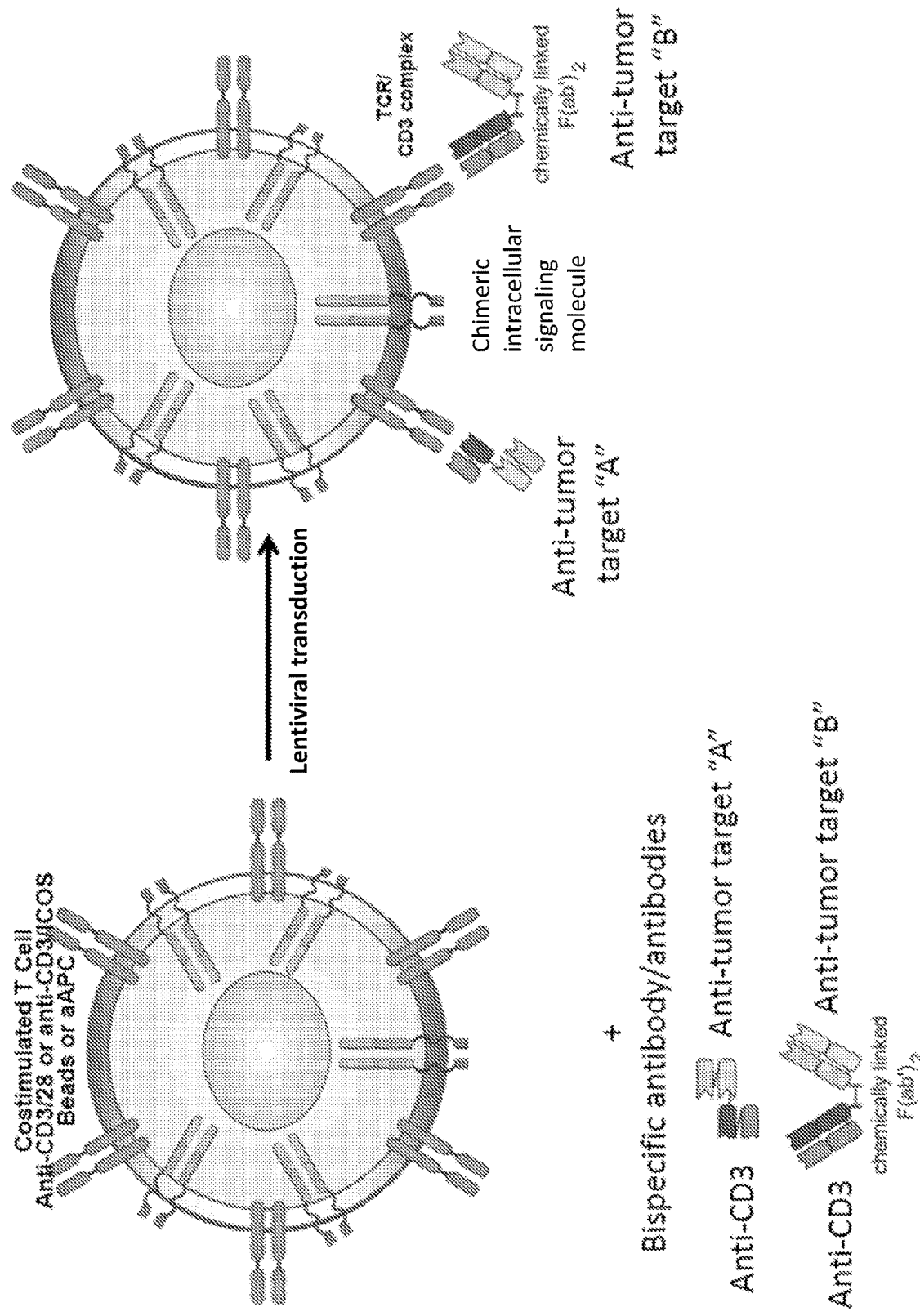
FIG. 13 is an illustration of a bispecific antibody armed T cell with a chimeric intracellular signaling molecule introduced by lentiviral vector.

The chimeric intracellular signaling molecule may also be introduced by lentiviral vector (FIG. 13) or mRNA electroporation (FIG. 14) into T cells. Similar to CART cells, chimeric intracellular signaling molecule modified T cells may display bispecific scFv or be coupled with bispecific antibodies through protein loading or arming just prior to infusion into the patient.

Figure 14:
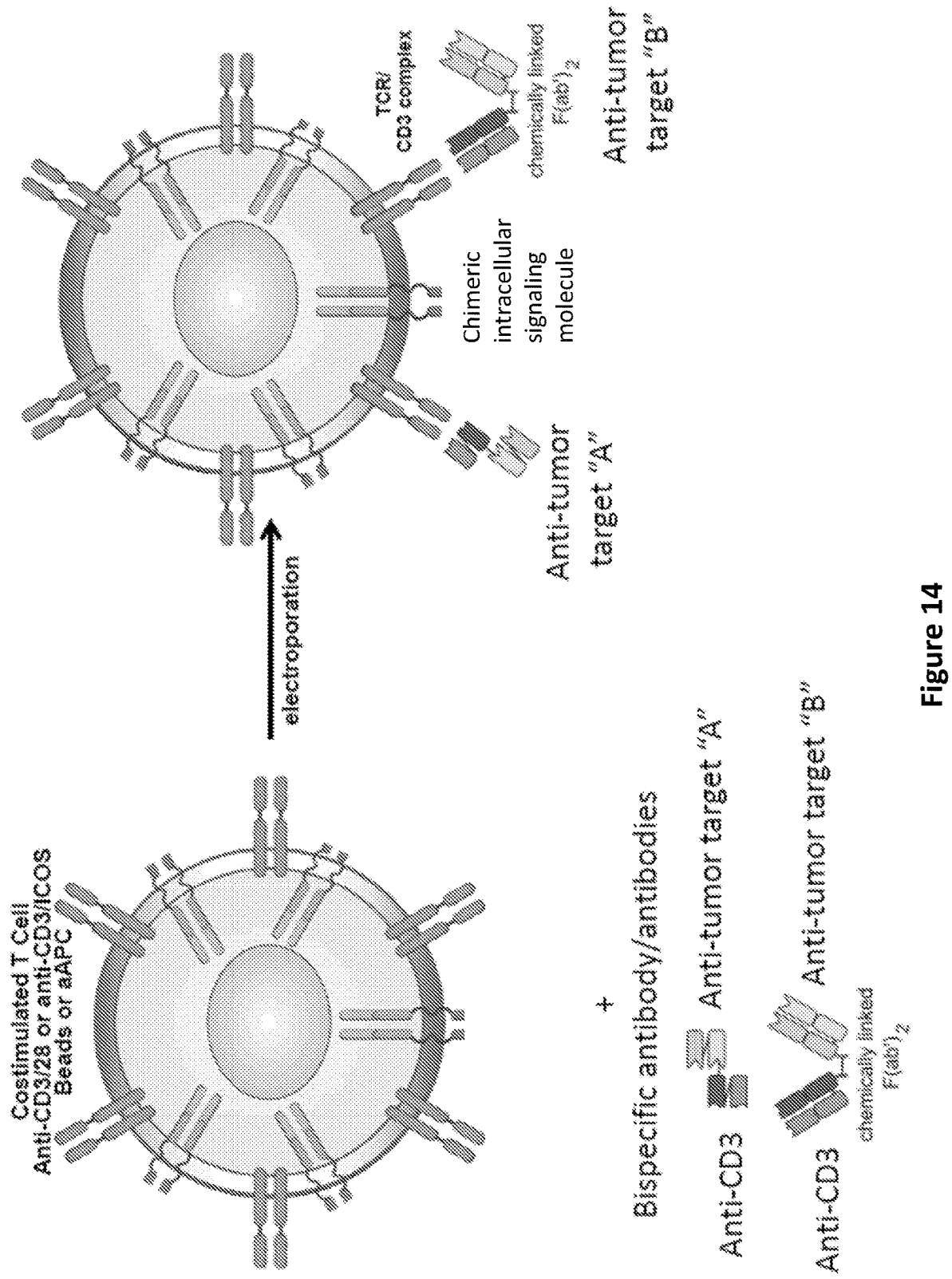
FIG. 14 is an illustration of a bispecific antibody armed T cell with a chimeric intracellular signaling molecule introduced by mRNA electroporation.

The chimeric intracellular signaling molecule may also be introduced into the T cells through mRNA electroporation (FIG. 14). In vitro transcribed mRNA is electroporated into the T cells prior to infusion into the patient to arm the T cells with bispecific scFv or bispecific antibodies.

Figure 15:
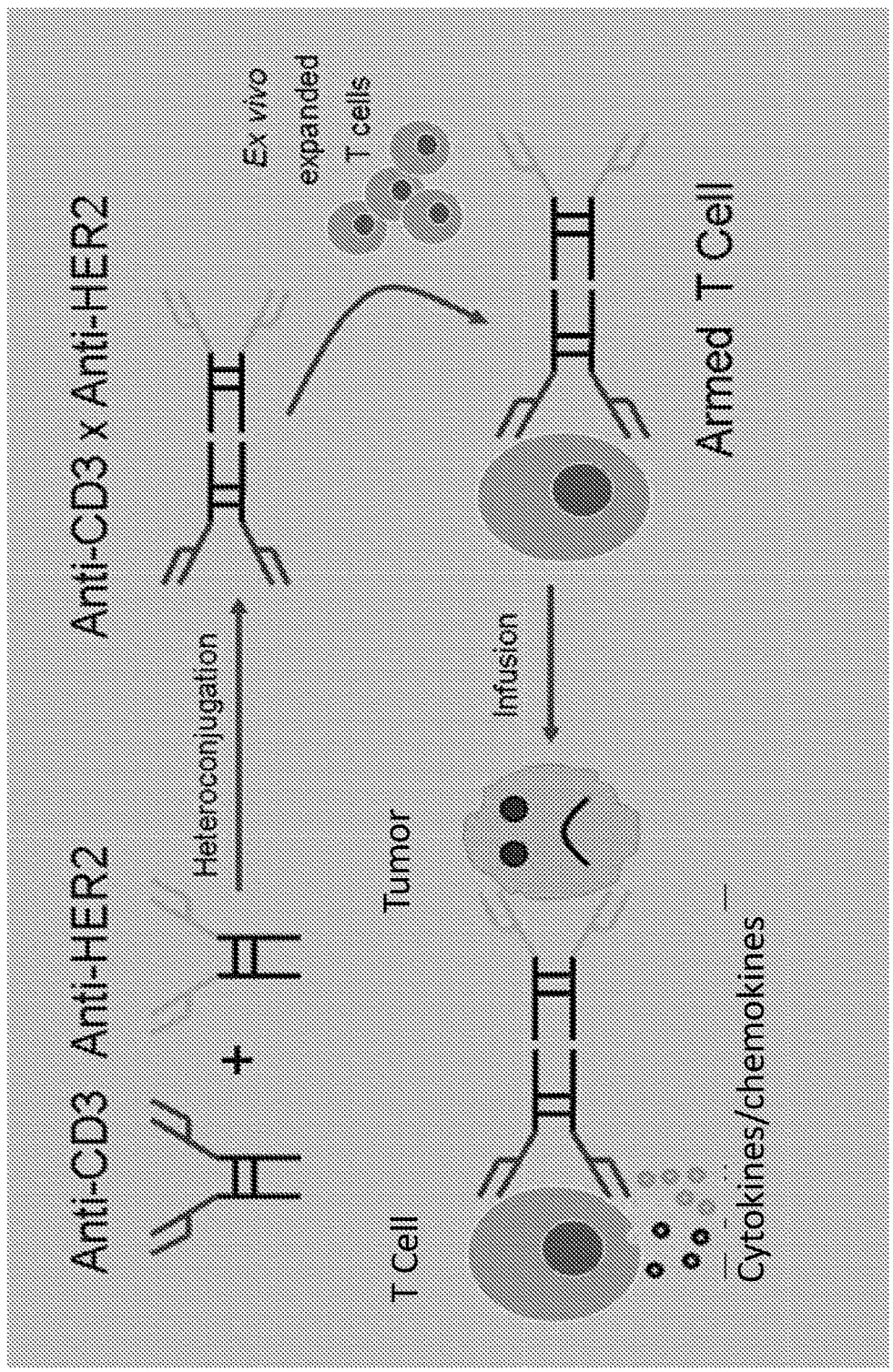
FIG. 15 is an illustration diagramming the enhanced effect arming T cells with bispecific antibodies has on the ability to kill target cells. The tumor microenvironment was modified through the release of Th$_1$ cytokines and chemokines that inhibited T regulatory cells (T$_{regs}$) and myeloid derived suppressor cells (MDSC) populations and recruited endogenous immune cells to become cytotoxic memory effector cells and memory B cells that produced antibody directed at tumor.

T cells armed with bispecific antibodies (BiAb) are hypothesized to exhibit enhanced cytotoxicity against target cells. FIG. 15 illustrates the mechanism of arming T cells with bispecific antibodies produced by chemical heteroconjugation of anti-CD3 (muromonab-CD3, OKT3) and specificity of the bispecific antibodies to any antigen (tumor, viral, bacterial or parasitic) of choice. Arming the T cells with bispecific antibodies should reactivate the armed T cells to exhibit non-MHC restricted cytotoxicity against target cells. The bispecific antibody armed T cells would then produce cytokines and chemokines upon engagement with the target cell.

Figure 16:
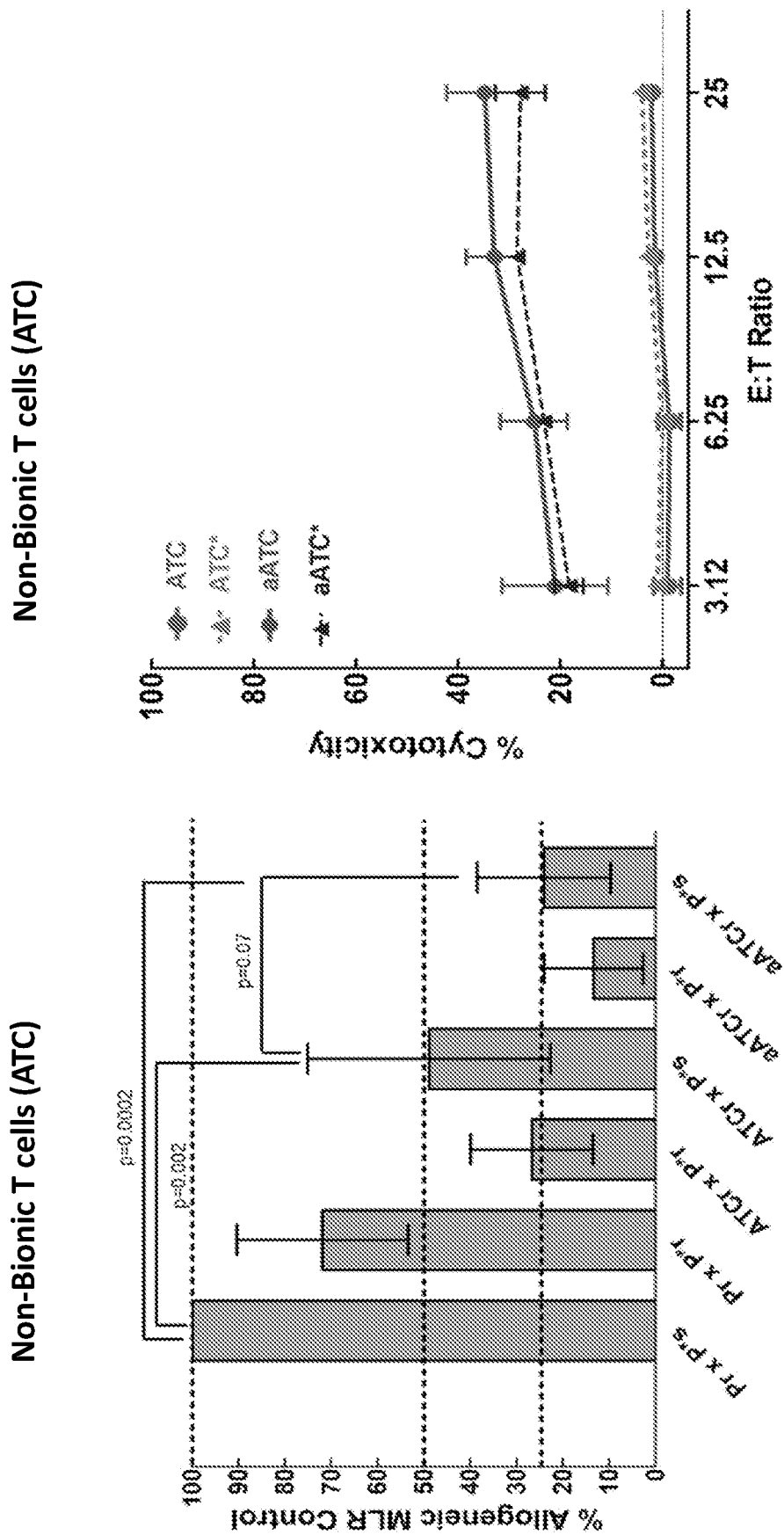
FIG. 16 is a panel of graphs showing that irradiation of bispecific antibody armed T cells blocked allogeneic responses (left graph) but did not inhibit cytotoxicity (right graph) when the armed T cells were bound to tumor targets. "r" signifies responder cells, "s" signifies stimulator cells and * signifies irradiated cells.

Irradiation of bispecific antibody armed T cells blocked allogeneic responses (left graph of FIG. 16) but did not inhibit cytotoxicity (right graph of FIG. 16) of armed T cell when bound to tumor targets. "r" signifies responder cells, "s" signifies stimulator cells and * signifies irradiated cells.

Figure 17:
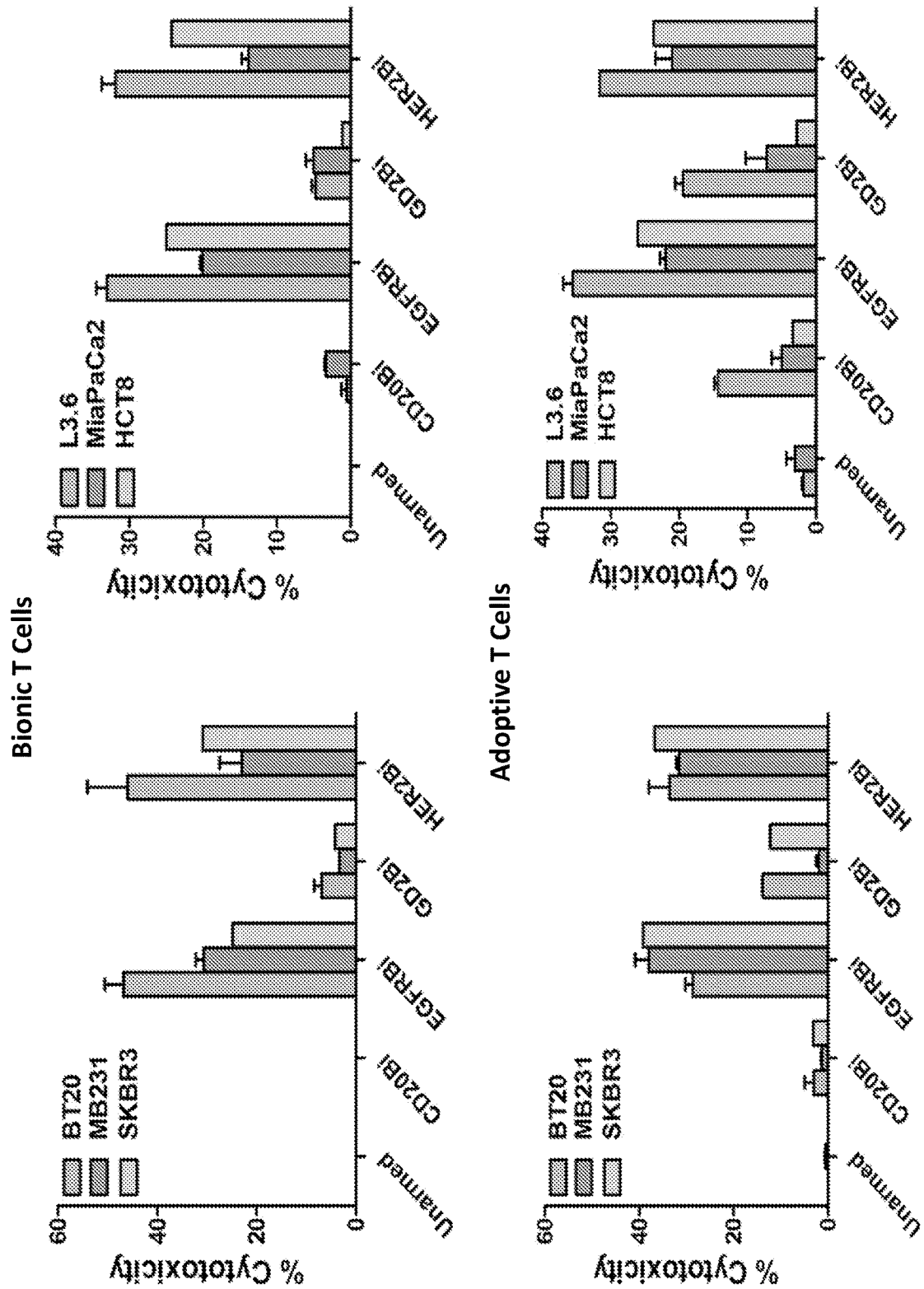
FIG. 17 is a panel of graphs showing specific cytotoxicity of unarmed or anti-CD20 bispecific antibody (CD20Bi), anti-EGFR bispecific antibody (EGFRBi), anti-GD2 bispecific antibody (GD2Bi) and anti-HER2 bispecific antibody (HER2Bi) armed metabolically enhanced T cells in a $^{51}Cr$ release assay against HER2 and EGFR expressing breast cancer and pancreatic/colorectal cancer cell lines. Assays were performed in triplicate using armed or unarmed T cells at effector/target ratio of 10:1 for 18 hours to measure cytotoxicity.

Specific cytotoxicity of unarmed or anti-CD20 bispecific antibody (CD20Bi), anti-EGFR bispecific antibody (EGFRBi), anti-GD2 bispecific antibody (GD2Bi) and anti-HER2 bispecific antibody (HER2Bi) armed metabolically enhanced T cells in a $^{51}$Cr release assay against HER2 and EGFR expressing breast cancer and pancreatic/colorectal cancer cell lines are shown in FIG. 17. Assays were performed in triplicate using armed or unarmed metabolically enhanced T cells at effector/target ratio of 10:1 for 18 hours to measure cytotoxicity.

Figure 18:
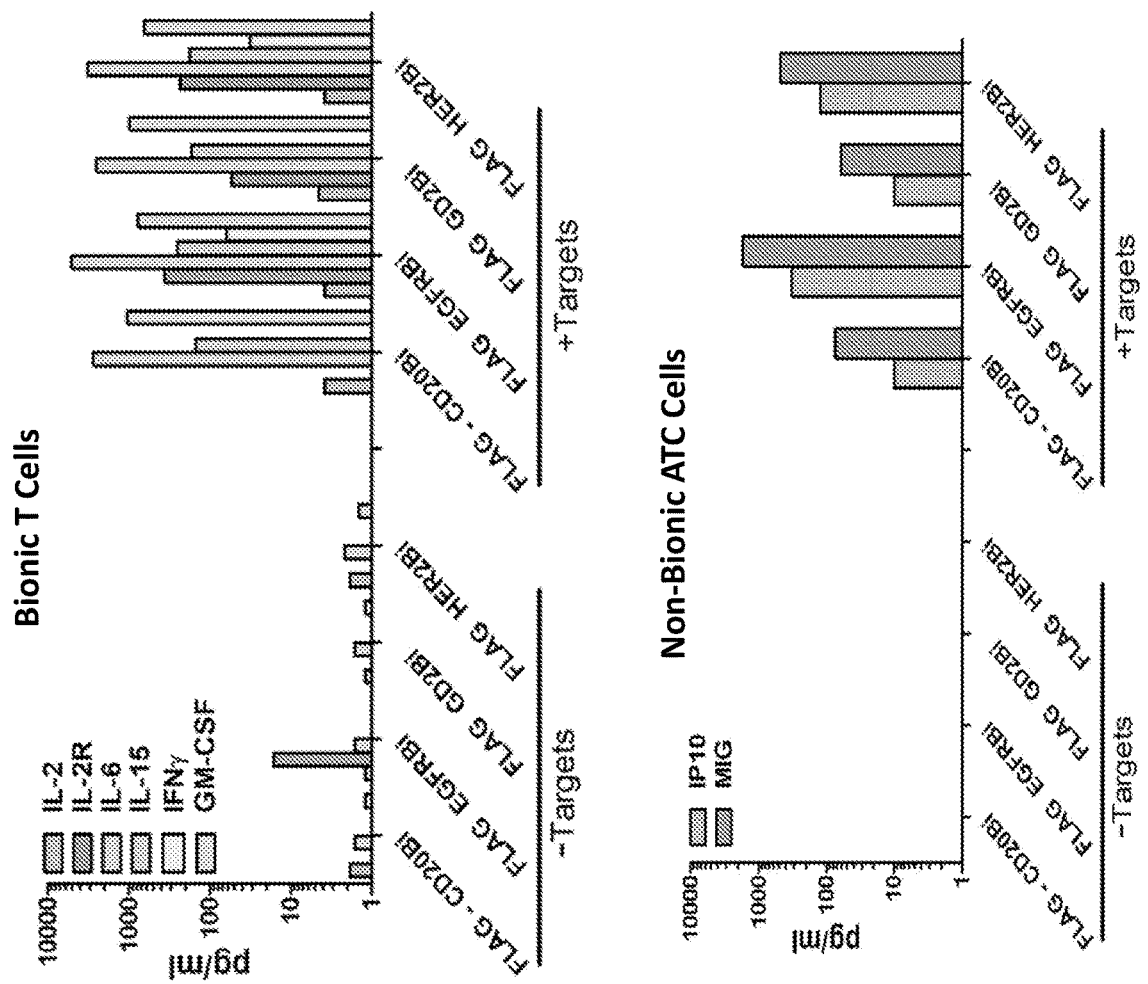
FIG. 18 is a panel of graphs showing the cytokine profile in culture supernatants. Unarmed or armed T cells or non-metabolically enhanced ATC were incubated overnight without target cells or with target cells (SKBR3) at E:T=10:1. The values are reported as pg/ml. The culture supernatant was assayed by Bio-Plex assay for the presence of cytokines (top graph) and chemokines (bottom graph).

Unarmed or armed T cells or non-metabolically enhanced ATC were incubated overnight without targets or with target cells (SKBR3) at E:T=10:1. The culture supernatant was assayed by Bio-Plex assay for the presence of cytokines (top graph of FIG. 18) and chemokines (bottom graph of FIG. 18). The values were reported as pg/ml.

Figure 19A:
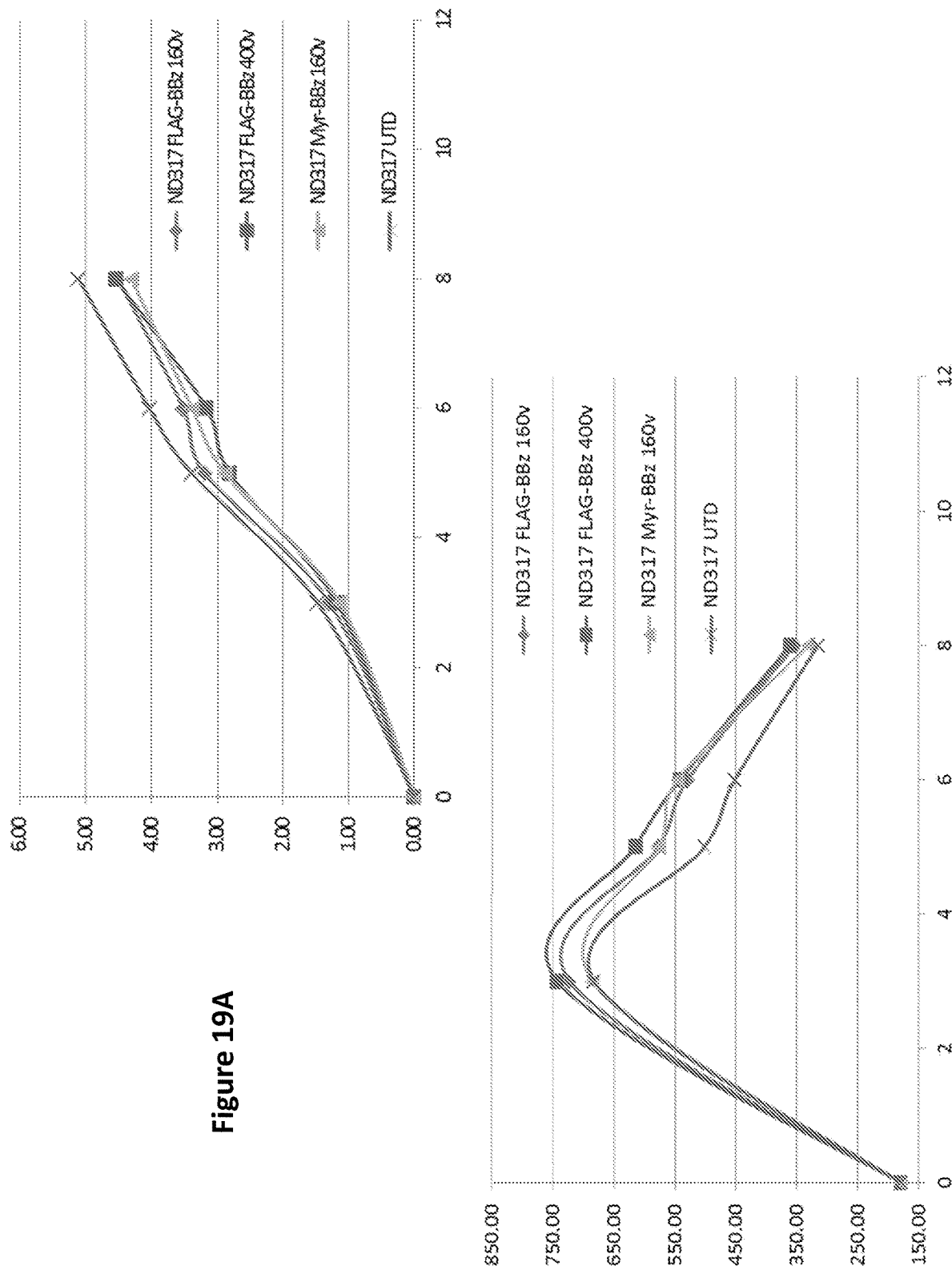
FIG. 19A is a panel of graphs showing expansion of T cells expressing flag-tagged chimeric intracellular signaling molecules, a CD8 transmembrane domain with 4-1BB and CD3zeta intracellular domains or a membrane-anchored myristoylated 4-1BB and CD3zeta intracellular domains.
Figure 19B:
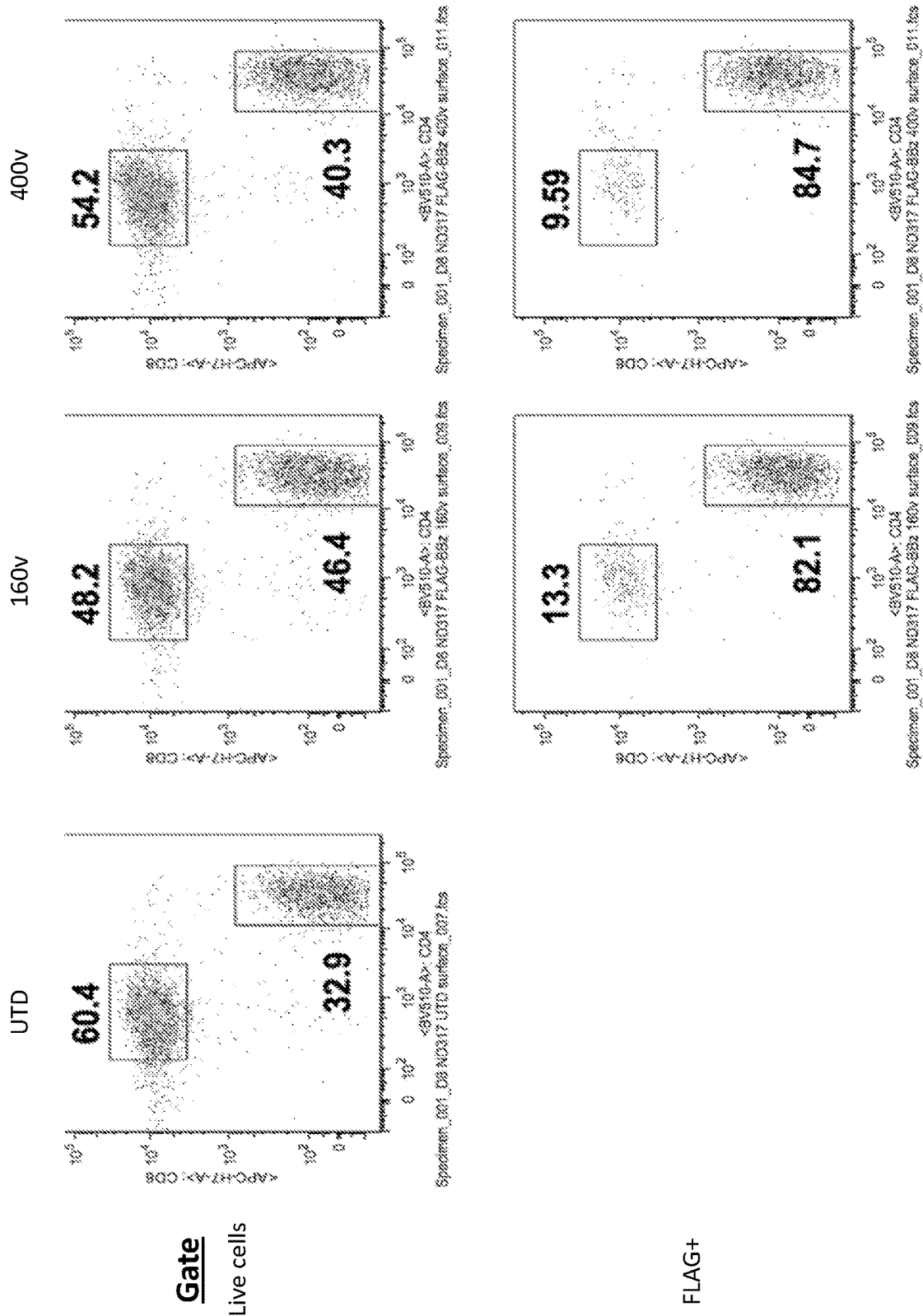
FIG. 19B is a panel of graphs showing enhancement of CD4 expression in T cells expressing flag-tagged chimeric intracellular signaling molecules. Normal donor ND317 T cells were activated with anti-CD3/28 beads and transduced to express the chimeric intracellular signaling molecule. These cells were greatly enhanced in CD4 populations.

To determine if expression of chimeric intracellular signaling molecules metabolically enhanced T cells, normal donor ND317 T cells were transduced with 160 μl or 400 μl virus to express flag-tagged chimeric intracellular signaling molecules including a CD8 transmembrane domain with 4-1BB and CD3zeta intracellular domains. The result of this transduction was a slightly slower expansion rate (slower decrease of cell size and doublings) (FIG. 19A). The metabolically enhanced T cells expressing flag-tagged chimeric intracellular signaling molecules were enriched for CD4+ cells. (FIG. 19B). The T cells expressing the flag-tagged chimeric intracellular signaling molecule diminished in percentage of overall population from day 6 to 8 (FIG. 19C).

Figure 19C:
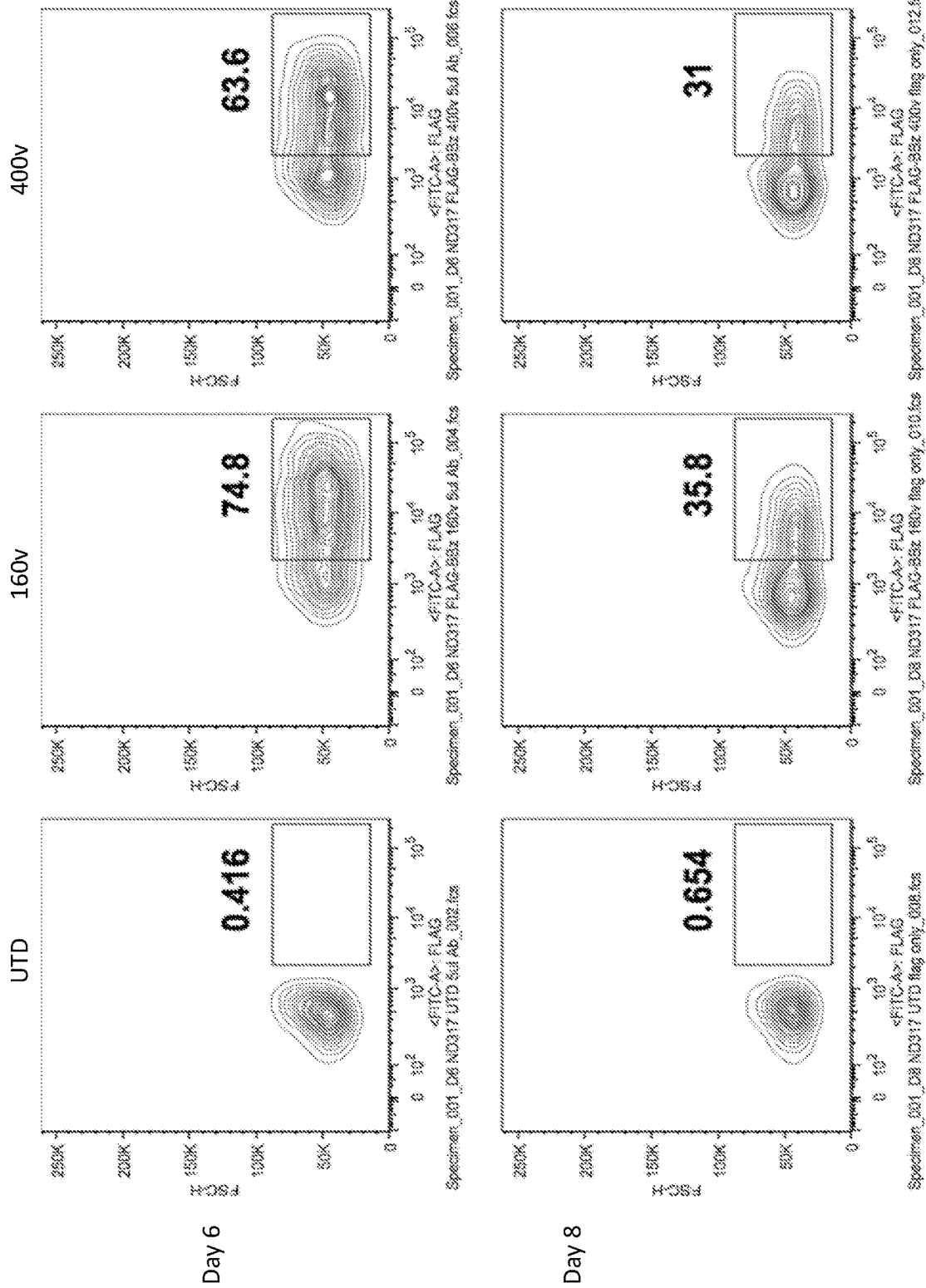
FIG. 19C is a panel of graphs showing transduction with 160 µl or 400 µl virus and expansion of flag-tagged chimeric intracellular signaling molecules, a CD8 transmembrane domain with 4-1BB and CD3zeta intracellular domains, in T cells. Normal donor ND317 T cells were transduced with flag-tagged chimeric intracellular signaling molecules. T cells expressing the flag-tagged chimeric intracellular signaling molecule diminished in percentage of overall population from day 6 to 8. '160 v' means 160 µl virus per $1e^6$ cells at initial transduction.

Expansion profiles of T cells expressing flag-tagged chimeric intracellular signaling molecules, a CD8 transmembrane domain with 4-1BB and CD3zeta intracellular domains or a membrane-anchored myristoylated 4-1BB and CD3zeta intracellular domains, are shown in FIG. 19C.

Figure 20:
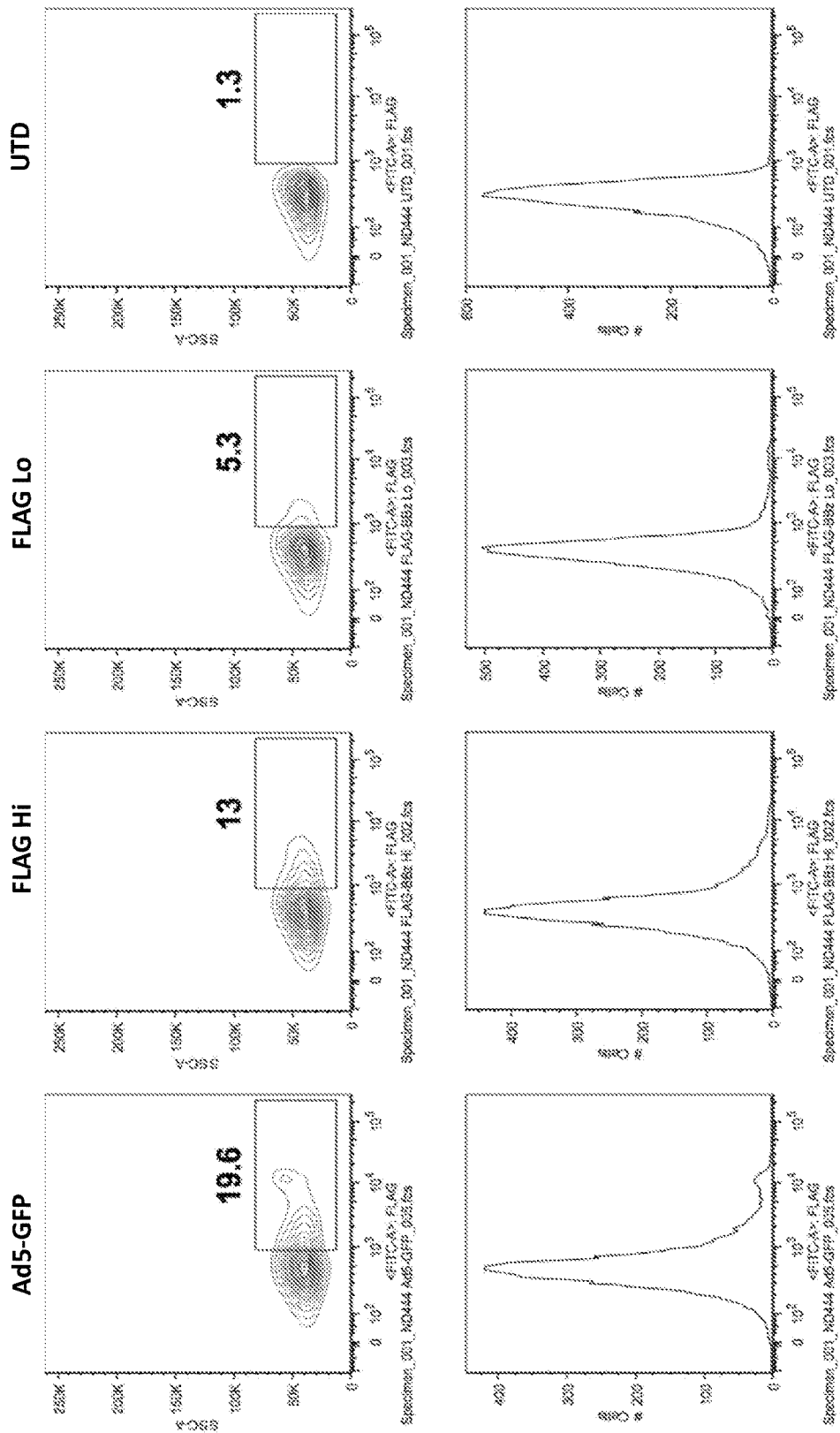
FIG. 20 is a panel of graphs showing characterization of normal donor ND444 T cells transduced with high (50%) and low (15%) viral amounts to express different percentages of the chimeric intracellular signaling molecules. Detection of flag-tagged T cells was lost over time.

Normal donor ND444 T cells transduced at high (50%) and low (15%) viral amounts are shown in FIG. 20. Detection of flag-tagged T cells was lost over time. However, metabolically enhanced T cells expressing (Flag+) were enriched for CD4+ cells.

Figure 21A:
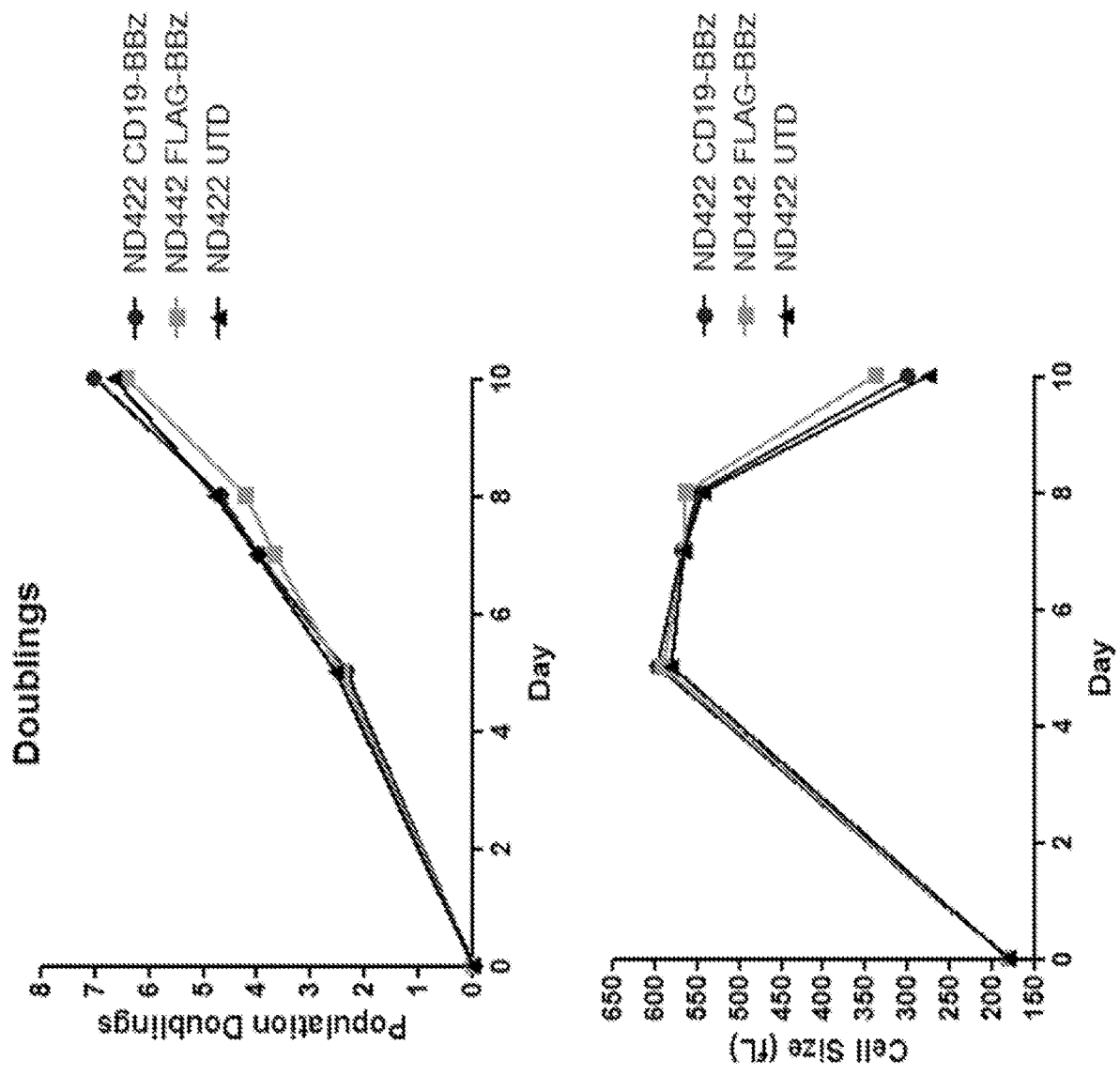
FIG. 21A is a panel of graphs showing expansion by population doublings and cell size of normal donor ND422 T cells transduced with a flag-tagged chimeric intracellular signaling molecule (BBz) or CAR19BBz. T cells are activated by CD3×28 beads, transduced and expansion monitored by coulter counter measurements and show similar profiles until cells become rested.
Figure 21B:
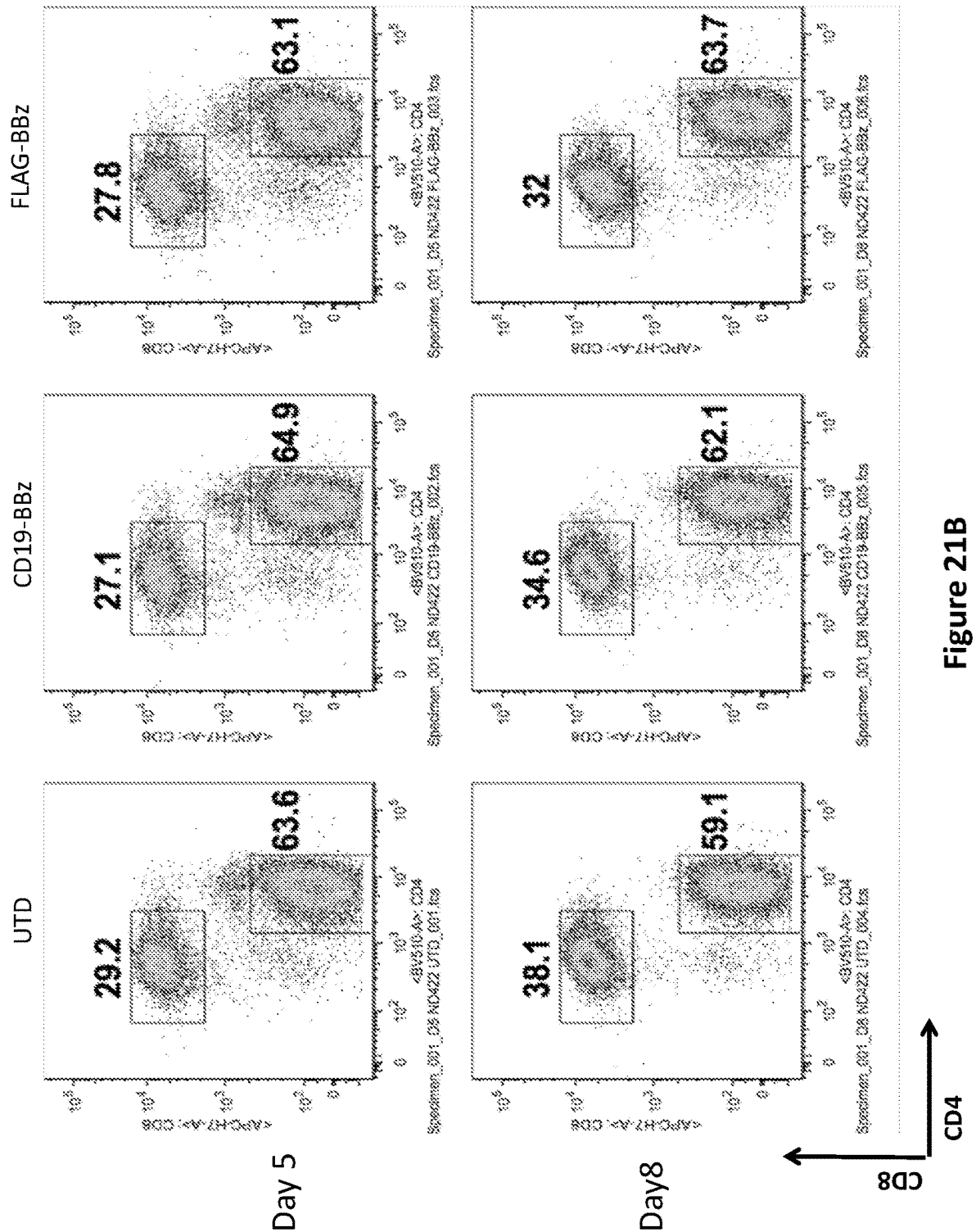
FIG. 21B is a panel of graphs showing CD4 and CD8 expression characterized on day 5 and day 8 on normal donor ND422 T cells transduced with flag-tagged chimeric intracellular signaling molecule (BBz) or CAR19BBz. The overall T cell population showed a biased CD4 expansion without any observed additional enhancement of CD4+ cells by chimeric intracellular signaling molecules. All data shown were gated on live CD3+ cells.
Figure 21C:
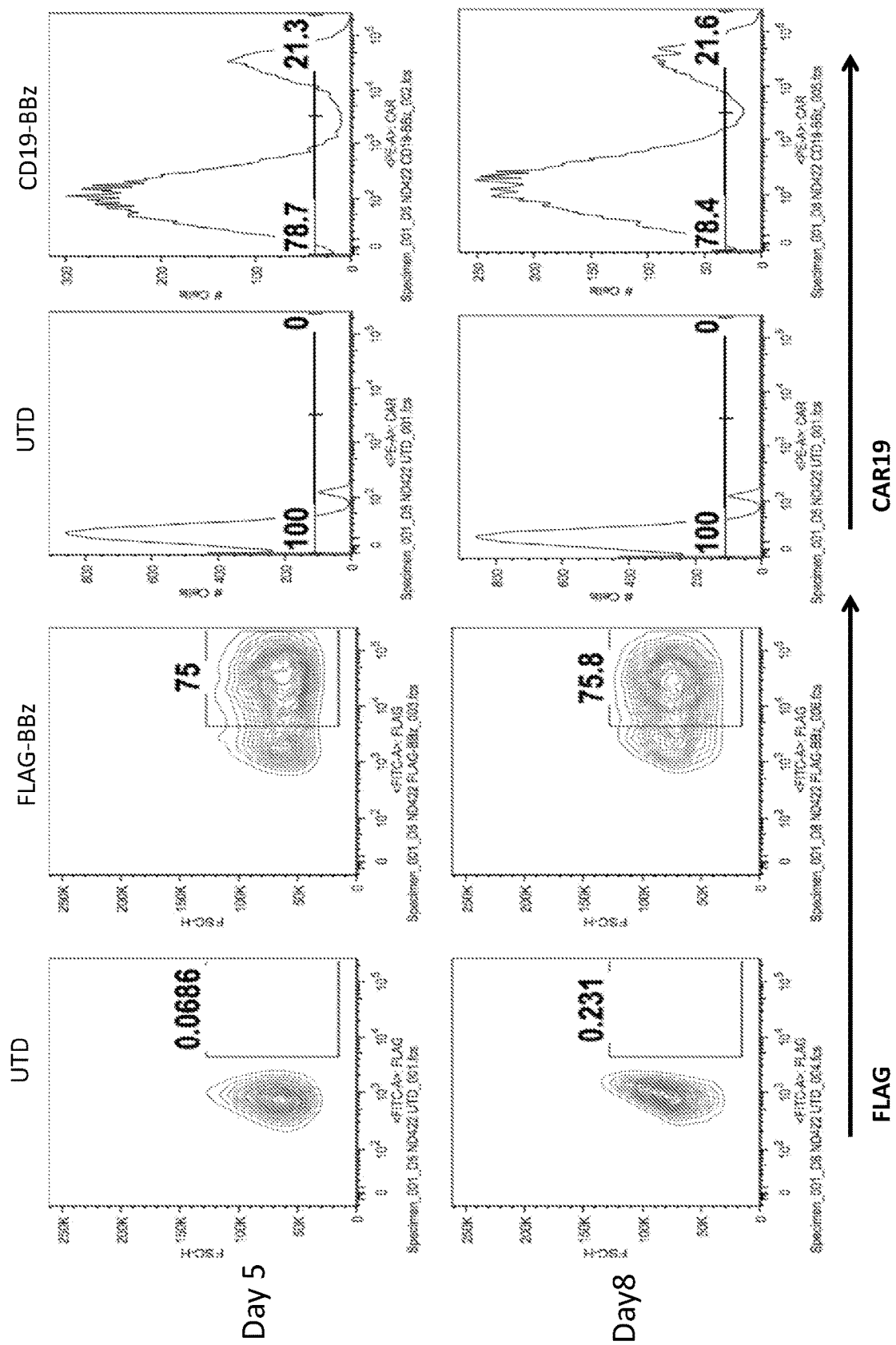
FIG. 21C is a panel of graphs showing no loss in the percentages of flag-tagged T cells from day 5 to day 8 of the normal donor ND422 T cells transduced with flag-tagged chimeric intracellular signaling molecule (BBz) or CAR19BBz.

Expansion of normal donor ND422 T cells was compared between cells transduced with a flag-tagged chimeric intracellular signaling molecule (BBz) or CAR19BBz (FIG. 21A). A slightly slower population doubling rate and cell size decrease was seen in FLAG-BBz transduced cells. The percentage of CD4 background expression was high for this donor, as seen by untransduced at day 5. A slight % in CD4 population was observed by Day 8 (FIG. 21B). However, this donor showed no loss in percentage of flag-tagged T cells was observed from day 5 to day 8 (FIG. 21C).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of metabolically enhancing a tumor specific T cell, comprising:
introducing a first nucleic acid encoding a chimeric antigen receptor (CAR) into a T cell in vitro to obtain a CAR T cell, wherein the CAR comprises an antigen binding domain that binds to CD19, a transmembrane domain, and intracellular signaling domains of a 4-1BB molecule and a CD3zeta molecule;
arming the CAR T cell in vitro with a bispecific antibody, wherein arming the CAR T cell comprises introducing a second nucleic acid encoding the bispecific antibody into the CAR T cell, wherein the bispecific antibody binds CD3 on the CAR T cell, and wherein the bispecific antibody is capable of binding to an antigen on a tumor cell in vivo; and
administering the armed CAR T cell to a CD19+ subject wherein the intracellular signaling domain is activated, thereby metabolically enhancing the tumor specific T cell.

2. The method of claim 1, wherein introducing the first nucleic acid comprises electroporating the first nucleic acid into the cell, wherein the first nucleic acid comprises an mRNA.

3. The method of claim 1, wherein the antigen is HER2, epidermal growth factor receptor (EGFR), or CD20.

4. The method of claim 1, wherein the bispecific antibody comprises an anti-CD3 antibody.

5. The method of claim 1, wherein the bispecific antibody comprises a first antibody chemically heteroconjugated to a second antibody, wherein the first antibody is specific to the antigen, and wherein the second antibody is specific to the CD3.

6. The method of claim 1, wherein introducing the second nucleic acid comprises electroporating the second nucleic acid into the cell, wherein the second nucleic acid comprises an mRNA.

7. The method of claim 1 further comprising irradiating the armed CAR T cell with up to 2500 rad, wherein said irradiation is sufficient to inhibit proliferation of the armed CAR T cell but is insufficient to inhibit cytokine secretion or cytotoxicity.

8. The method of claim 1, wherein the CAR comprises the sequence of SEQ ID NO: 1.

* * * * *